US012558467B2

(12) United States Patent
Chiaki et al.

(10) Patent No.: US 12,558,467 B2
(45) Date of Patent: Feb. 24, 2026

(54) BLOOD PURIFICATION APPARATUS

(71) Applicant: Nikkiso Co., Ltd., Tokyo (JP)

(72) Inventors: Hikaru Chiaki, Shizuoka (JP); Yuya Menjoh, Shizuoka (JP); Kazuya Tsuji, Shizuoka (JP); Kunihiko Akita, Shizuoka (JP)

(73) Assignee: Nikkiso Co., Ltd., Tokyo (JP)

( * ) Notice: Subject to any disclaimer, the term of this patent is extended or adjusted under 35 U.S.C. 154(b) by 432 days.

(21) Appl. No.: 18/014,620

(22) PCT Filed: Jun. 7, 2021

(86) PCT No.: PCT/JP2021/021630
§ 371 (c)(1),
(2) Date: Jan. 5, 2023

(87) PCT Pub. No.: WO2022/009583
PCT Pub. Date: Jan. 13, 2022

(65) Prior Publication Data
US 2023/0270923 A1 Aug. 31, 2023

(30) Foreign Application Priority Data

Jul. 9, 2020 (JP) ................................. 2020-118793

(51) Int. Cl.
*A61M 1/16* (2006.01)
(52) U.S. Cl.
CPC ........ *A61M 1/1647* (2014.02); *A61M 1/1605* (2014.02); *A61M 1/165* (2014.02)
(58) Field of Classification Search
CPC .. A61M 1/1647; A61M 1/1605; A61M 1/165; A61M 1/3646; A61M 1/3649;

(Continued)

(56) References Cited

U.S. PATENT DOCUMENTS

| | | | | |
|---|---|---|---|---|
| 2016/0250405 A1* | 9/2016 | Kogoshi | ............. | A61M 1/3649 |
| | | | | 210/321.72 |
| 2018/0036470 A1* | 2/2018 | Hasegawa | ............. | A61M 1/301 |

FOREIGN PATENT DOCUMENTS

| JP | 2009131412 A | 6/2009 |
|---|---|---|
| JP | 2013-106976 A | 6/2013 |

(Continued)

OTHER PUBLICATIONS

Futamura Hiroshi; Yokoyama Kazumi; Toyoda Masahiro; Ito Yoshihiro, Blood Purifying Apparatus, 2009, Espacenet Translation (Year: 2009).*

(Continued)

*Primary Examiner* — Nicholas J. Weiss
*Assistant Examiner* — Brandon W. Levy
(74) *Attorney, Agent, or Firm* — Young Basile Hanlon & MacFarlane, P.C.

(57) ABSTRACT

A blood circuit and a dialysate circuit bidirectionally circulate a fluid through a blood purification membrane of a blood purifier, and include a first flow route that causes a dialysate to flow from the dialysate circuit into the blood circuit through a connection flow route connecting the dialysate circuit to the blood circuit while bypassing the blood purifier, and a second flow route that causes the dialysate to flow from the dialysate circuit into the blood circuit through the blood purification membrane. The controller performs control such that blood in the blood circuit is returned to the body by feeding the dialysate to one of these flow routes, determine if a flow amount of the dialysate reaches a predetermined flow amount, and control such that the blood in the blood circuit is returned to the body by feeding the dialysate to the other one of these flow routes.

11 Claims, 13 Drawing Sheets

(58) Field of Classification Search
　　　CPC ...... A61M 1/365; A61M 1/3652; A61M 1/16;
　　　　　　　　　　A61M 2205/3331; A61M 2205/3334;
　　　　　　　　　　A61M 1/36225; A61M 1/3643; A61M
　　　　　　　　　　1/3626; A61M 1/267; A61M 1/3413;
　　　　　　　　　　　　A61M 2202/0413; A61M 60/37
　　　See application file for complete search history.

(56)　　　　　　　　References Cited

FOREIGN PATENT DOCUMENTS

| | | | |
|---|---|---|---|
| JP | 5205036 | B2 * | 6/2013 |
| JP | 2014-188219 | A | 10/2014 |
| JP | 5914106 | B2 | 5/2016 |
| JP | 2019-187789 | A | 10/2019 |
| WO | 2014/199949 | A2 | 12/2014 |

OTHER PUBLICATIONS

European Search Report for Application No. 21838753.8, dated Nov. 3, 2023, 7 pgs.
Office Action issued in corresponding JP Application No. 2020-118793, issued Oct. 17, 2023, and its English translation, 6 pgs.
European Official Communication: Office Action for Application No. 21838753.8, dated Apr. 30, 2024, 6 pgs.
International Preliminary Report on Patentability for Application No. PCT/JP2021/021630, form IB338, dated Jan. 10, 2023, 5 pgs.
International Preliminary Report on Patentability for Application No. PCT/JP2021/021630, form IB326, dated Jan. 10, 2023, 5 pgs.
Chinese First Office Action issued in Application No. 202180048627.2 with its English translation, dated Apr. 23, 2025, 18 pgs.

* cited by examiner

BLOOD PURIFICATION APPARATUS

CROSS-REFERENCE TO RELATED APPLICATION(S)

This application is a national stage application of International Application No. PCT/JP2021/021630, filed on Jun. 7, 2021, which claims priority to Japanese Application No. 2020-118793, filed on Jul. 9, 2020.

TECHNICAL FIELD

The present disclosure relates to a blood purification apparatus and more specifically a blood purification apparatus that returns blood in a blood circuit to a body.

BACKGROUND ART

In a case where kidneys that constitute part of organs of a human do not operate normally (a renal failure), functions to produce urine out of extra water in the body, to excrete unwanted waste products in the body, and so forth do not work well. To deal with the renal failure, a dialysis apparatus is used for conducting a treatment to extracorporeally circulate blood from a patient and to filter waste products and water in the blood by using a blood purifier (a hemodialysis treatment, hereinafter referred to as a dialysis treatment).

The dialysis apparatus is configured to withdraw blood from a patient, to introduce the blood into a blood purifier (a blood flow route) through a blood circuit while introducing a dialysate from a supply source of the dialysate into the blood purifier (a dialysate flow route) through a dialysate circuit at the same time, to purify the blood by exchanging components such as waste products and electrolytes between the blood and the dialysate through the blood purifier, and to return the purified blood to the patient. Since the blood remains in the blood circuit after the introduction of the blood into the blood circuit in the dialysis treatment, an operation to return the remaining blood to the body of the patient (blood return) is generally carried out.

As the above-described blood return method, there is known a method of introducing a dialysate (or normal saline) into a blood circuit through a connection line (a rehydration line) that connects a dialysate circuit to the blood circuit while bypassing a blood purifier, and returning blood to a body by causing the dialysate to push out the blood in the blood circuit. This method will be referred to as a first blood return process (a rehydration method). Meanwhile, there is also known a method of introducing a dialysate from a dialysate circuit into a blood circuit through a filtration membrane of a blood purifier, and returning blood to a body by causing the dialysate to push out the blood in the blood circuit. This method will be referred to as a second blood return process (a back filtration method).

CITATION LIST

Patent Literature

PTL 1: Japanese Patent Laid-Open No. 2019-187789

SUMMARY OF INVENTION

PTL 1 discloses a technique for carrying out rehydration by back filtration and carrying out the rehydration by using a rehydration line depending on a state of permeability of a filtration membrane in a blood purifier. However, a rehydration operation disclosed in PTL 1 is designed to complementarily adopt the rehydration using the rehydration line in combination on the premise of the rehydration by the back filtration. For this reason, there may be a case of a failure to effectively exert respective advantages of the rehydration by the back filtration and the rehydration using the rehydration line.

A blood purification apparatus according to the present embodiment is a blood purification apparatus including: a blood circuit and a dialysate circuit configured to bidirectionally circulate a fluid through a blood purification membrane of a blood purifier; and a controller. Here, the blood circuit and the dialysate circuit include a first flow route that causes a dialysate to flow from the dialysate circuit into the blood circuit through a connection flow route that connects the dialysate circuit to the blood circuit while bypassing the blood purifier, and a second flow route that causes the dialysate to flow from the dialysate circuit into the blood circuit through the blood purification membrane. The controller performs control such that blood in the blood circuit is returned to a body by feeding the dialysate to one of the first flow route and the second flow route. The controller determines whether or not a flow amount of the dialysate reaches a predetermined flow amount. The controller performs control such that the blood in the blood circuit is returned to the body by feeding the dialysate to the other one of the first flow route and the second flow route in response to determination that the flow amount of the dialysate reaches the predetermined flow amount.

A blood purification apparatus according to another embodiment is a blood purification apparatus including: a blood circuit and a dialysate circuit configured to bidirectionally circulate a fluid through a blood purification membrane of a blood purifier; and a controller. Here, the blood circuit and the dialysate circuit include a first flow route that causes a dialysate to flow from the dialysate circuit into the blood circuit through a connection flow route that connects the dialysate circuit to the blood circuit while bypassing the blood purifier, and a second flow route that causes the dialysate to flow from the dialysate circuit into the blood circuit through the blood purification membrane. The controller performs control such that blood in the blood circuit is returned to a body by feeding the dialysate to one of the first flow route and the second flow route. The controller determines whether or not a return flow amount of the blood reaches a predetermined blood return amount. The controller performs control such that the blood in the blood circuit is returned to the body by feeding the dialysate to the other one of the first flow route and the second flow route in response to determination that the blood return amount of the blood reaches the predetermined blood return amount.

The blood purification apparatus according to the embodiment makes it possible to effectively exert respective advantages of the first blood return process and the second blood return process.

DESCRIPTION OF EMBODIMENTS

Figure 1:
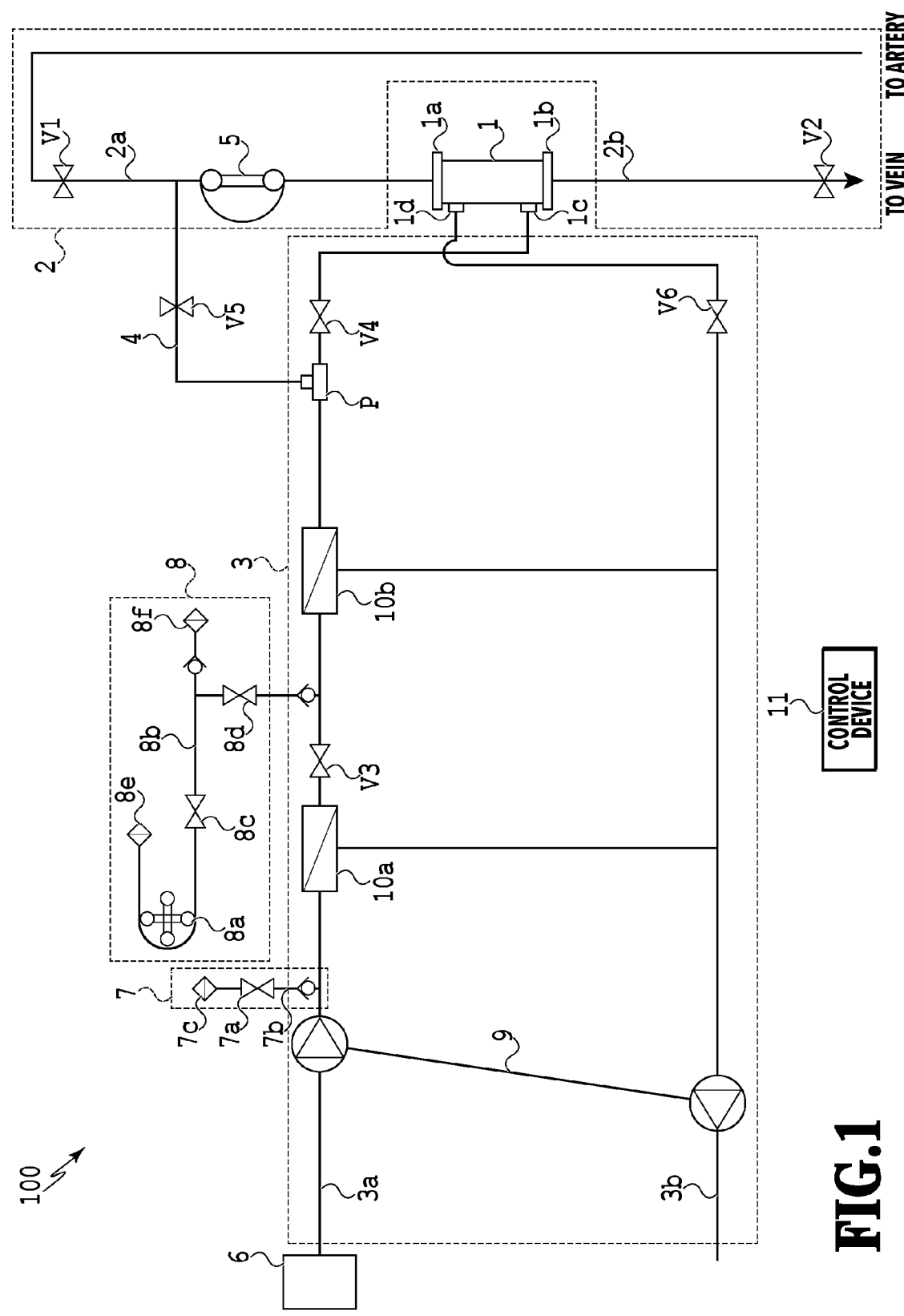
FIG. 1 is an overall configuration diagram of a dialysis apparatus according to a first embodiment.

Dialysis apparatuses (blood purification apparatuses) according to embodiments will be described below with reference to the drawings. A dialysis apparatus according to each embodiment switches and carries out a first blood return process (a rehydration method) and a second blood return process (a back filtration method) in order to return blood remaining in a blood circuit to a body. The aforementioned processes of blood return to the body are called blood return processes, which are mainly carried out after a dialysis treatment.

In the first blood return process, a dialysate flows in a dialysate circuit and runs from the dialysate circuit to a blood circuit. According to this flow of the dialysate, the dialysate flows in a blood flow route (an inner side of a blood purification membrane) provided in a blood purifier, thereby pushing out blood remaining in the blood circuit and the blood purifier and returning the blood to a body. On the other hand, in the second blood return process, the dialysate flows in the dialysate circuit and runs from the dialysate circuit to the blood purifier. According to this flow of the dialysate, the dialysate passes through a dialysate flow route (an outer side of the blood purification membrane) in the blood purifier, whereby the dialysate pushes out the blood through pores in the blood purification membrane and the blood is returned to the body. Here, in the first blood return process and the second blood return process, both of the fluids are partially mixed together in the process that the dialysate pushes out the blood.

The blood flows in the blood flow route of the blood purifier during the dialysis treatment. Due to this flow of the blood, the pores in the blood purification membrane or the blood flow route may be partially occluded with proteins such as albumin in the blood. In the first blood return process, the dialysate flows in the blood flow route as with the blood in the course of the dialysis treatment. Accordingly, in the case where the blood flow route in the blood purifier is occluded, it is difficult for the dialysate to flow in the blood circuit in the first blood return process. As a consequence, it is not possible to achieve sufficient blood return. On the other hand, in the second blood return process, the dialysate runs through the dialysate flow route in the blood purifier. Accordingly, it is possible to achieve sufficient blood return as compared to the first blood return process.

In the second blood return process, the dialysate flows from the dialysate flow route to the inner side of the blood purification membrane. In the second blood return process, a larger amount of the dialysate is mixed with the blood because of a large contact area between the dialysate and the blood as compared to the first blood return process. Accordingly, in the second blood return process, the larger amount of the dialysate may be taken into the body, which is undesirable in some cases. This means that the first blood return process can perform the blood return by using a smaller amount of the dialysate as compared to the second blood return process. The dialysis apparatuses of the embodiments deal with the above-mentioned drawbacks of the first blood return process and the second blood return process.

First Embodiment

FIG. 1 is a block diagram showing a configuration of a dialysis apparatus 100 according to a first embodiment. The dialysis apparatus 100 includes a blood purifier 1, a blood circuit 2, a dialysate circuit 3, a rehydration circuit 4, a blood pump 5, a dialysate supplier 6, a primary air introducer 7, a secondary air introducer 8, a dual pump 9, a dialysate filter 10*a*, a dialysate filter 10*b*, and a controller 11 as main constituents. The constituents shown in FIG. 1 merely represent examples of constituents for implementing the present embodiment, and a chamber for trapping bubbles of the blood flowing in the blood circuit 2, and the like are also disposed in reality.

The blood purifier 1, which is also referred to as a dialyzer, purifies blood of a patient. The blood purifier 1 includes a blood introduction inlet 1*a* that introduces the blood from the blood circuit 2, and a blood introduction outlet 1*b* that discharges the purified blood. Moreover, the blood purifier 1 includes a dialysate introduction inlet 1*c* that introduces a dialysate from the dialysate circuit 3, and a dialysate drainage port 1*d* that drains the dialysate (drainage). A blood purification membrane is provided inside the blood purifier 1. The blood purification membrane is formed from a bundle of hollow fibers having pores on side surfaces (a hollow fiber membrane). An inner side of the blood purification membrane (the hollow fibers) is a blood flow route and an outer side of the blood purification membrane (the hollow fibers) is a dialysate flow route. The blood to flow in the blood purifier 1 flows in the blood flow route and unwanted substances such as uremic substances are removed by passing through the pores in the blood purification membrane by one or both of diffusion and ultrafiltration. The dialysate to flow in the blood purifier 1 flows in the dialysate flow route and the blood is supplemented only with substances such as electrolytes included in the dialysate, which are necessary for a human body, by passing through the pores. Here, it is also possible to use the inner side of the hollow fibers as the dialysate flow route and to use the outer side of the hollow fibers as the blood flow route.

The blood circuit 2 and the dialysate circuit 3 bidirectionally circulate the fluids (the blood and the dialysate) through the blood purification membrane of the blood purifier 1. The blood circuit 2 is a flow route where the blood removed from the patient is introduced into the blood purifier 1 and the blood discharged from the blood purifier 1 (the purified blood) is returned to the patient (the blood flows in a direction indicated with an arrow in the blood circuit 2 of FIG. 1). The blood circuit 2 is mainly formed from a tube that enables passage of the blood. The blood circuit 2 includes a blood removal side circuit 2*a* and a blood return side circuit 2*b*.

The blood removal side circuit 2*a* is a flow route where the blood removed from the patient is introduced into the blood purifier 1. One end of the blood removal side circuit 2*a* is attached to a blood removal side puncture needle (not shown) that is punctured into a blood vessel of the patient, and another end thereof is joined to the blood introduction inlet 1*a*. An on-off valve (a Solenoid valve) V1 is disposed at the blood removal side circuit 2*a*. A flow of the blood in the blood removal side circuit 2*a* is controlled by opening and closing the on-off valve V1. The blood return side circuit 2*b* is a flow route where the blood discharged from the blood purifier 1 is returned to the patient. One end of the blood return side circuit 2*b* is attached to a blood return side puncture needle (not shown) that is punctured into a blood vessel of the patient, and another end thereof is joined to the blood introduction outlet 1*b*. An on-off valve (a Solenoid valve) V2 is disposed at the blood return side circuit 2*b*. A flow of the blood in the blood return side circuit 2*b* is controlled by opening and closing the on-off valve V2.

The blood pump 5 is disposed at the blood removal side circuit 2*a* and configured to feed the fluids in the blood circuit 2 in a direction of movement from the blood removal side circuit 2*a* to the blood return side circuit 2*b* (hereinafter referred to as a normal direction in delivering liquid) or in a direction of movement from the blood return side circuit 2*b* to the blood removal side circuit 2*a* (hereinafter referred to as a reverse direction in delivering liquid). Moreover, the blood pump 5 is formed from a peristaltic pump that includes a stator and a rotor. By the forward rotation of the rotor, the blood removal side circuit 2*a* pinched between the stator and the rotor is squeezed so as to generate the flow in the normal direction in delivering liquid. Meanwhile, by the reverse rotation of the rotor, the blood removal side circuit 2*a* is squeezed so as to generate the flow in the reverse direction in delivering liquid. The blood pump 5 is provided with a rotary encoder (not shown). The rotary encoder detects the number of rotations of the rotor.

The dialysate circuit 3 is a flow route that supplies the dialysate to the blood purifier 1 and/or the blood circuit 2, and discharges the drainage of the dialysate from the blood purifier 1. The dialysate circuit 3 is mainly formed from a tube that enables passage of the dialysate. The dialysate circuit 3 includes a dialysate introduction circuit 3*a* and a dialysate drainage circuit 3*b*.

The dialysate introduction circuit 3*a* is a flow route from the dialysate supplier 6 to the dialysate introduction inlet 1*c*. The dialysate flows in the blood purifier 1 by way of the dialysate introduction circuit 3*a*. An on-off valve (a Solenoid valve) V3, an on-off valve (a Solenoid valve) V4, and a dialysate port P are disposed at the dialysate introduction circuit 3*a*. A flow of the dialysate into the blood purifier 1 is controlled by opening and closing the on-off valve V3 and the on-off valve V4. The dialysate port P takes out the dialysate.

The dialysate drainage circuit 3*b* is a flow route from the dialysate drainage port 1*d* to a dialysate drainer (not shown). The drainage from the blood purifier 1 is drained to the dialysate drainer by way of the dialysate drainage circuit 3*b*. An on-off valve (a Solenoid valve) V6 is disposed at the dialysate drainage circuit 3*b*. A flow of the drainage to the dialysate drainer is controlled by opening and closing the on-off valve V6.

The rehydration circuit 4 is a connection flow route that connects the blood circuit 2 to the dialysate circuit 3. Specifically, the rehydration circuit 4 is a flow route that supplies the dialysate from the dialysate circuit 3 to the blood circuit 2 while bypassing the blood purifier 1, which is a flow route from the dialysate port P to the blood removal side circuit 2*a*. The rehydration circuit 4 is used for the blood return of the blood in the blood circuit to the patient in accordance with the first blood return process. An on-off valve (a Solenoid valve) V5 is disposed at the rehydration circuit 4. A flow of the dialysate to the blood removal side circuit 2*a* is controlled by opening and closing the on-off valve V5.

The dialysate supplier 6 includes a chamber for generating the dialysate by mixing pure water (such as RO water) with an undiluted solution and storing the dialysate, and introduces the dialysate into the dialysate introduction circuit 3*a*. Here, the dialysate supplier 6 receives supply of the pure water from a not-illustrated pure water machine (an RO water machine) disposed outside the dialysis apparatus 100, and receives supply of (suctions) the undiluted solution from a not-illustrated undiluted solution tank externally mounted on the dialysis apparatus 100. While the dialysate supplier 6 generates the dialysate and introduces the dialysate into the dialysate introduction circuit 3*a* at normal times, generation of the new dialysate may be restricted in the event of a blackout and the like. In this case, the introduction of the dialysate from the dialysate supplier 6 into the dialysate introduction circuit 3*a* is stopped and the dialysate stored in the dialysate filter 10*a* and/or the dialysate filter 10*b* is introduced into the dialysate introduction circuit 3*a* instead. Details will be described later.

The primary air introducer 7 introduces air into the dialysate circuit 3, or more specifically, the (primary) dialysate filter 10*a* to be described later. The dialysate filter 10*a* is opened by the primary air introducer 7 and is set to an atmospheric pressure, and the dialysate stored inside the filter is fed to the dialysate port P. The primary air introducer 7 includes an on-off valve (a Solenoid valve) 7*a*, an air flow route 7*b*, and an air filter 7*c*. The on-off valve 7*a* is opened so as to introduce the air into the dialysate filter 10*a* through the air flow route 7*b*. The air filter 7*c* removes dust in the air.

The secondary air introducer 8 introduces the air into the dialysate circuit 3, or more specifically, the (secondary) dialysate filter 10*b* to be described later. The dialysate filter 10*b* is opened by the secondary air introducer 8 and is set to a positive pressure, and the dialysate stored inside the filter is fed to the dialysate port P. The secondary air introducer 8 includes a delivery pump 8*a*, an air flow route 8*b*, an on-off valve (a Solenoid valve) 8*c*, an on-off valve (a Solenoid valve) 8*d*, an air filter 8*e*, and an air filter 8*f*. The delivery pump 8*a* incorporates a rotor, and introduces the air into the dialysate filter 10*b* through the air flow route 8*b* by rotation of the rotor. A flow of the air to the dialysate filter 10*b* is controlled by opening and closing the on-off valve 8*c* and the on-off valve 8*d* disposed between the delivery pump 8*a* and the dialysate filter 10*b*. The air filter 8*e* and the air filter 8*f* remove dust in the air.

Note that the above-described primary air introducer 7 may have a configuration to include the delivery pump, the air flow route, and the on-off valves as with the secondary air introducer 8.

The dual pump 9 is disposed across the dialysate introduction circuit 3*a* and the dialysate drainage circuit 3*b*. The dual pump 9 introduces the dialysate to a downstream side in a fluid feeding direction of the dialysate introduction circuit 3*a*, and meanwhile, discharges the drainage of the dialysate to a downstream side in the fluid feeding direction of the dialysate drainage circuit 3b. Here, a plunger (not shown) is provided inside a housing of the dual pump 9. A volume on the dialysate introduction circuit 3a side and a volume on the dialysate drainage circuit 3b side are defined while interposing the plunger in between, and the introduction of the dialysate and the discharge of the drainage are interlocked with reciprocation of the plunger.

The dialysate filter 10a and/or the dialysate filter 10b purify the dialysate by trapping substances such as endotoxins contained in the dialysate. Meanwhile, in the dialysate filter 10a and the dialysate filter 10b, hollow fibers (a hollow fiber membrane) with side walls provided with pores are bundled together and put into a housing. The dialysate filter 10a and/or the dialysate filter 10b are formed such that the dialysate flows from a primary side (an inner side) to a secondary side (an outer side) of the hollow fiber membrane. The dialysate filter 10a and the dialysate filter 10b have a property of blocking passage of the air with surface tension of water molecules by passing water thereto. Note that the dialysate filter 10a and the dialysate filter 10b can store the dialysate inside the housing. On the other hand, the dialysate filter 10a and the dialysate filter 10b may be formed from a single filter instead of formation from two filters. In the meantime, the outer side of the hollow fiber membrane may be formed as the primary side and the inner side of the fiber membrane may be formed as the secondary side.

The controller 11 is a processing device that controls the entire dialysis apparatus 100 including the blood pump 5 and the on-off valves V1 to V6 mentioned above, and so forth. The controller 11 includes an arithmetic device and a storage device (a storage device such as a RAM and a ROM). The arithmetic device may be implemented by a processor such as a CPU and a microcontroller, an ASIC (application specific integrated circuit), an FPGA (field programmable gate array), and the like, but its mode is not limited.

Next, processing concerning the first embodiment will be described with reference to FIGS. 2 to 4. The first embodiment will describe an example of efficiently returning the blood in the blood purifier 1 and the blood circuit 2 to the body by carrying out the second blood return process after carrying out the first blood return process in the blood return process after the dialysis treatment. Moreover, the first embodiment will describe an example of carrying out the blood return by using the dialysate stored in the dialysate filter 10a and the dialysate filter 10b instead of introducing the new dialysate from the dialysate supplier 6. The dialysate in the dialysate filter 10a and the dialysate filter 10b is the dialysate that flowed and was stored in those filters in the dialysis treatment. In other words, the dialysate in the dialysate filter 10a and the dialysate filter 10b is the clean dialysate which was not used in the dialysis treatment.

Figure 2:
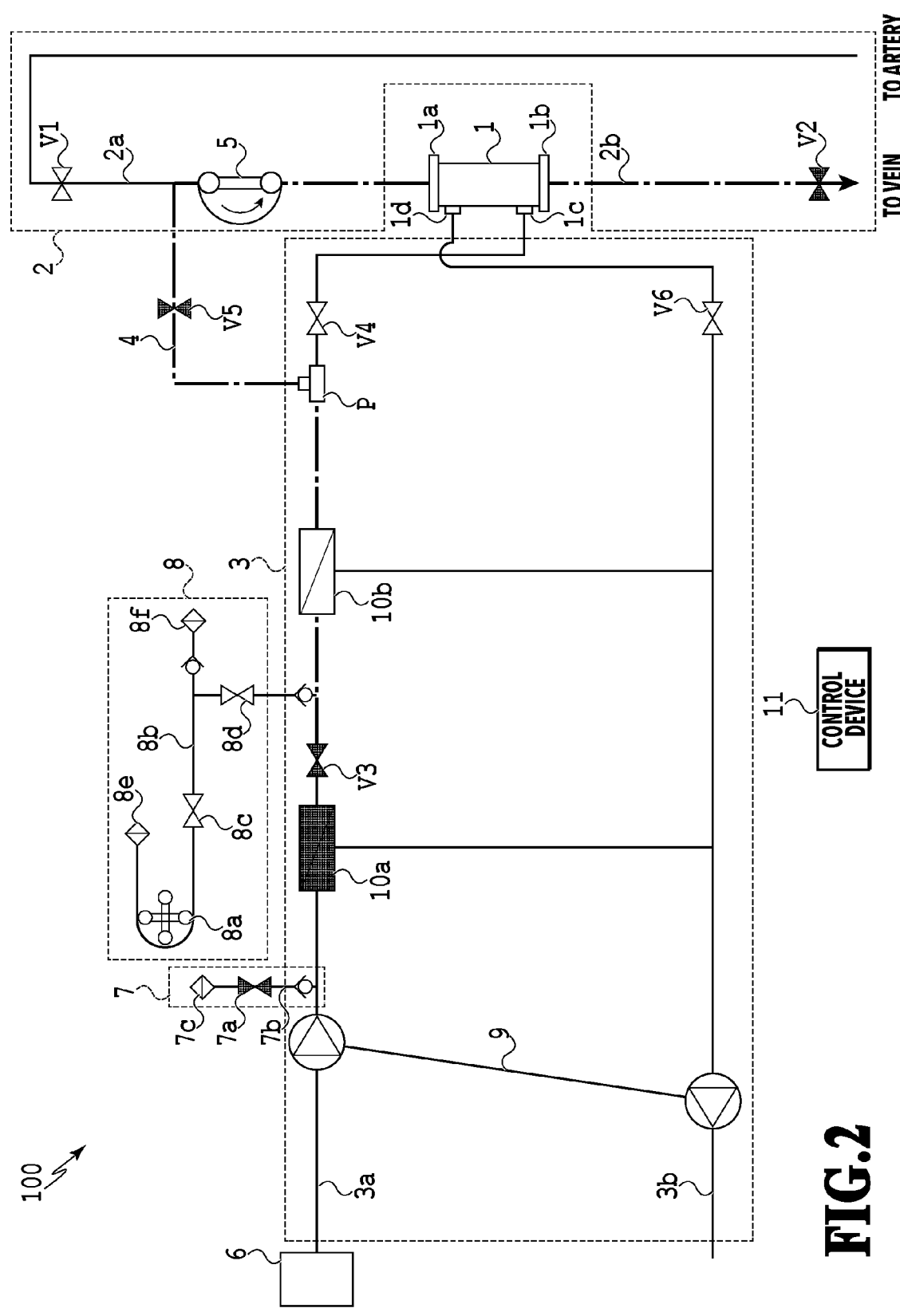
FIG. 2 is a diagram showing a flow of a dialysate in a first blood return process (a normal direction in delivering liquid)

FIG. 2 shows a flow of the dialysate in the first blood return process to be carried out in the first place in the blood return process. In the following drawings, on-off valves among the on-off valves (V1 to 6, 7a, 8c, and 8d) in the drawings are indicated with hatching in the case the on-off valves are opened, and the on-off valves in the drawings are indicated with outlines in the case where the on-off valves are closed.

As shown in FIG. 2, the on-off valve 7a, the on-off valve V3, the on-off valve V5, and the on-off valve V2 are opened in the first blood return process. Meanwhile, the blood pump 5 rotates forward. By opening the on-off valve 7a, the air is introduced into the dialysate filter 10a, and the dialysate filter 10a is set to the atmospheric pressure. Accordingly, the dialysate stored in the dialysate filter 10a flows in the dialysate introduction circuit 3a. By opening the on-off valve V3, the on-off valve V5, and the on-off valve V2 and by the forward rotation of the blood pump 5, the dialysate passes through the dialysate introduction circuit 3a, the rehydration circuit 4, the blood removal side circuit 2a, the blood purifier 1 (the blood flow route), and the blood return side circuit 2b. In FIG. 2, this flow of the dialysate is indicated with an arrow of a chain line. By this flow of the dialysate, the blood remaining in the blood purifier 1 and the blood circuit 2 is pushed out and is returned to the patient. Note that in the process where the dialysate pushes out the blood, these two fluids are partially mixed together in the first blood return process.

In the case where a predetermined amount of the dialysate flows from the dialysate filter 10a, the first blood return process is switched to the second blood return process. This switching is conducted by the controller 11, and details thereof will be described later. FIG. 3 shows a flow of the dialysate in the second blood return process.

Figure 3:
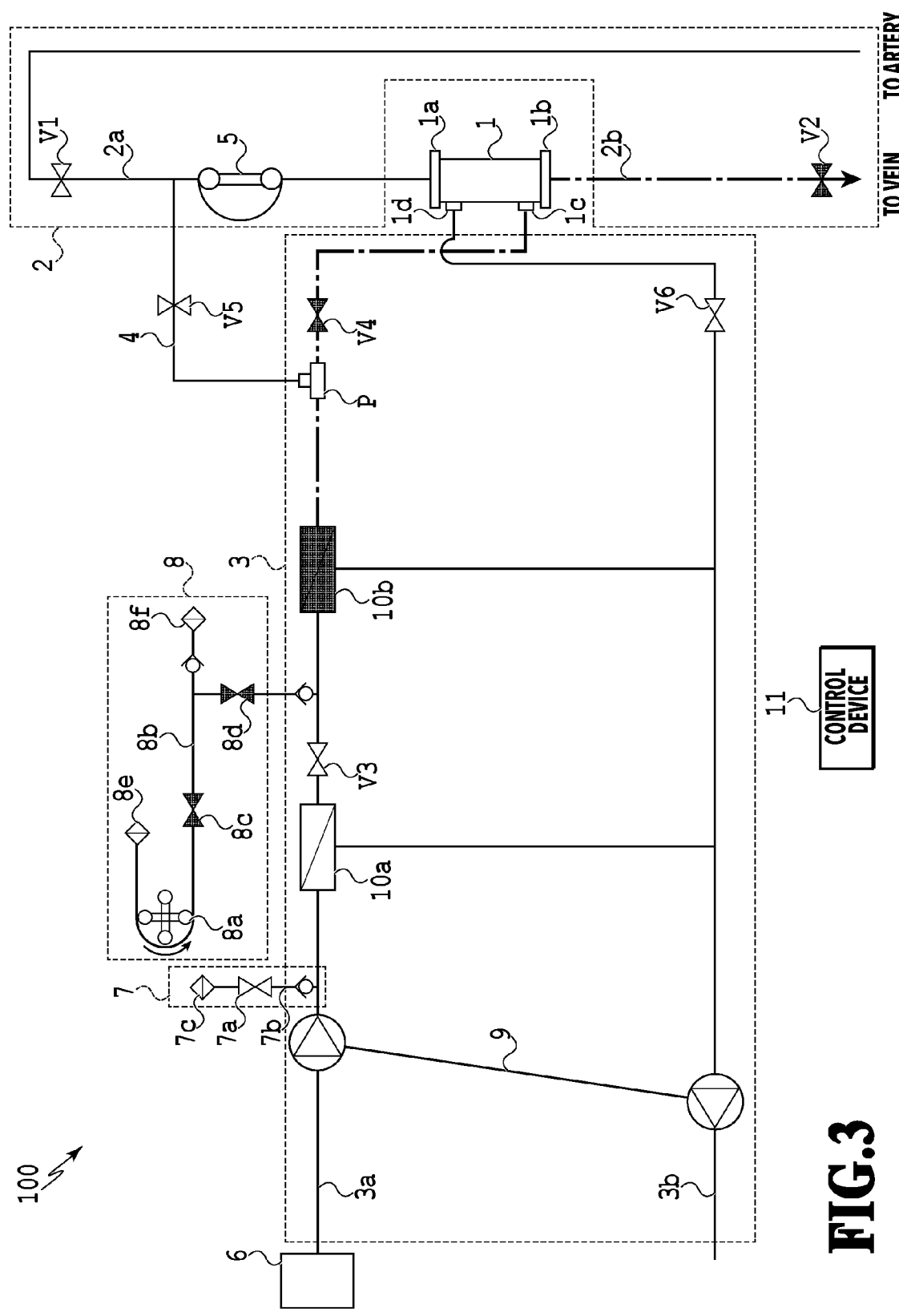
FIG. 3 is a diagram showing a flow of the dialysate in a second blood return process (the normal direction in delivering liquid)

As shown in FIG. 3, the on-off valve 7a, the on-off valve V3, and the on-off valve V5 are closed in the case where the first blood return process is switched to the second blood return process. Moreover, the blood pump 5 stops the rotation. The delivery pump 8a rotates instead. In the meantime, the on-off valve 8c, the on-off valve 8d, and the on-off valve V4 are opened. By the rotation of the delivery pump 8a and by opening the on-off valve 8c and the on-off valve 8d, the air is introduced into the dialysate filter 10b, and the dialysate filter 10b is set to the positive pressure. Accordingly, the dialysate stored in the dialysate filter 10b flows in the dialysate introduction circuit 3a. By opening the on-off valve V4 and by the rotation of the delivery pump 8a, the dialysate passes through the dialysate introduction circuit 3a, the blood purifier 1 (the blood purification membrane), and the blood return side circuit 2b. Here, the dialysate flows inside the blood purifier 1 in the order of the dialysate flow route, the blood purification membrane, and the blood flow route. In FIG. 3, this flow of the dialysate is indicated with an arrow of a chain line. By this flow of the dialysate, the dialysate pushes out the blood remaining in the blood purifier 1, and the blood is returned to the patient. Note that in the process where the dialysate pushes out the blood, these two fluids are partially mixed together in the second blood return process. Here, an amount of mixture of the dialysate and the blood in the second blood return process is larger than an amount of mixture of the dialysate and the blood in the first blood return process. Accordingly, the first blood return process is desirable from the viewpoint of an amount of use of the dialysate.

As described above, it is possible to carry out the blood return in the first blood return process by using a smaller amount of the dialysate as compared to the second blood return process. On the other hand, in the second blood return process, it is not possible to carry out the sufficient blood return in the case where the blood purifier 1 (the blood flow route) is occluded (a fluid feeding amount per unit time is reduced due to the occlusion of the blood flow route). In the second blood return process, the dialysate flows in the dialysate flow route and returns the blood remaining in the blood purifier 1 to the patient. In the first embodiment, a predetermined amount of the dialysate is fed to the blood circuit 2 by carrying out the first blood return process in the first place, thereby returning the blood remaining in the blood circuit 2 and the blood purifier 1 to the body. Thereafter, the second blood return process is carried out so as to return the blood remaining in the blood purifier 1 to the body. This processing makes it possible to return the blood remaining in the blood circuit 2 to the patient by using the smaller amount of the dialysate, and to return the blood remaining in the occluded blood purifier 1 (the blood flow route) to the patient thereafter.

Next, the processing according to the first embodiment will be described with reference to FIG. 4. The processing shown in FIG. 4 is executed in accordance with an instruction of the controller 11. In the present embodiment, the second blood return process is carried out after carrying out the first blood return process. An amount of the dialysate necessary for carrying out the first blood return process and an amount of the dialysate necessary for carrying out the second blood return process are assumed to be determined at a prescribed proportion in advance. In the following, the amount of the dialysate necessary for carrying out the first blood return process will be referred to as a "first dialysate amount" and the amount of the dialysate necessary for carrying out the second blood return process will be referred to as a "second dialysate amount". The first dialysate amount is an empirically obtained value, which may be set based on the volume of the dialysate filter 10a, for example. Likewise, the second dialysate amount is an empirically obtained value, which may be set based on the volume of the dialysate filter 10b, for example.

Meanwhile, an amount of blood return to be returned to the body in the first blood return process and an amount of blood return to be returned to the body in the second blood return process may be determined at a prescribed proportion in advance based on priming volumes of the blood purifier 1 and the blood circuit 2, for example. In the following, the amount of blood return to be returned to the body in the first blood return process will be referred to as a "first blood return amount" and the amount of blood return to be returned to the body in the second blood return process will be referred to as a "second blood return amount". The priming volumes may be determined in advance for the blood purifier 1 and the blood circuit 2, respectively. Meanwhile, in a dialysis treatment, the priming volumes may be measured based on time from a point of blood removal from the patient to a point of blood return to the patient through the blood purifier 1 and the blood circuit 2, and on an amount of rotations (detected with the encoder) of the blood pump 5 during that time. Alternatively, the priming volumes may be measured by gauging the time from the blood removal to the blood return by using detection of the blood with a blood evaluation device or a blood thickness sensor (not shown) disposed at the blood circuit 2 as a trigger. Here, the blood evaluation device is a detector that evaluates whether or not the fluid flowing in the blood circuit 2 is the blood, and the blood thickness sensor is a sensor that measures the thickness of the blood flowing in the blood circuit 2.

First, the controller 11 instructs the primary air introducer 7 to introduce the air into the dialysate filter 10a (step S401). In response to this instruction, the on-off valve 7a of the primary air introducer 7 is opened and the dialysate filter 10a is set to the atmospheric pressure. Accordingly, the dialysate stored in the dialysate filter 10a can flow in the dialysate introduction circuit 3a (to be more precise, the dialysate flows by the rotation of the blood pump 5).

Next, the controller 11 instructs the on-off valves (the on-off valve V3, the on-off valve V5, and the on-off valve V2) for carrying out the first blood return process to be opened (step S402). The on-off valve V3, the on-off valve V5, and the on-off valve V2 are opened in response to this instruction.

Next, the controller 11 instructs the blood pump 5 to rotate forward (step S403). The blood pump 5 rotates forward in response to this instruction. By the processing in steps S401 to S403, the dialysate passes through the dialysate introduction circuit 3a, the rehydration circuit 4, and the blood purifier 1 (the blood flow route), thus pushing out the blood that remains in the blood purifier 1 (the blood flow route) and the blood circuit 2 and returning the blood to the body (the first blood return process).

Next, the controller 11 determines whether or not a flow amount of the dialysate flowing in the dialysate circuit 3 reaches the first dialysate amount (step S404). The processing in step S404 is repeated until the flow amount of the dialysate reaches the first dialysate amount.

Here, in a case where the first dialysate amount exceeds the volume of the dialysate filter 10a, the dialysate stored in the dialysate filter 10b also needs to be used for carrying out the first blood return process. In this case, the dialysate needs to be fed out of the dialysate filter 10b by switching from the dialysate filter 10a to the dialysate filter 10b. While the present embodiment explains an example of feeding the dialysate from the dialysate filter 10a in the first place, the dialysate may be fed from the dialysate filter 10b in the first place instead. In this case, the dialysate stored in the dialysate filter 10a may also be used, and the dialysate needs to be fed out of the dialysate filter 10a by switching from dialysate filter 10b to the dialysate filter 10a.

In order to switch from the dialysate filter 10a to the dialysate filter 10b, the controller 11 first determines that the dialysate flowing in the dialysate circuit 3 reaches a predetermined amount (such as the volume of the dialysate filter). Thereafter, the controller 11 instructs the on-off valve 7a to be closed, and instructs the delivery pump 8a, the on-off valve 8c, and the on-off valve 8d to rotate and to be opened, respectively.

On the other hand, in order to switch from the dialysate filter 10b to the dialysate filter 10a, the controller 11 first determines that the dialysate flowing in the dialysate circuit 3 reaches a predetermined amount (such as the volume of the dialysate filter). Thereafter, the controller 11 instructs the delivery pump 8a to stop the rotation, instructs the on-off valve 8c and the on-off valve 8d to be closed, and instructs the on-off valve 7a to be opened.

The processing to determine whether or not the flow amount of the dialysate flowing in the dialysate circuit 3 reaches the first dialysate amount may include detecting that a pressure between the dialysate filter 10b and the dialysate port P or inside the blood circuit 2 turns into a negative pressure, for example. Because, owing to the property of the dialysate filter 10a that blocks the passage of the air after passing the water thereto, the dialysate does not flow after reaching the first dialysate amount despite the rotation of the blood pump 5 (suctioning) even in the case where the air is introduced from the primary air introducer 7 into the dialysate filter 10a, and the inside of the closed circuit turns into the negative pressure. In this case, a pressure gauge is provided between the dialysate filter 10b and the dialysate port P or in the blood circuit 2, for example, and the pressure gauge detects the pressure of the air. The detected pressure value is transmitted to the controller 11.

Meanwhile, the processing to determine whether or not the flow amount of the dialysate flowing in the dialysate circuit 3 reaches the first dialysate amount may include measuring a temperature of the air introduced from the primary air introducer 7 and a temperature of a flow route (from the primary air introducer 7 to the dialysate filter 10a) of the dialysate introduction circuit 3a, and detecting whether or not the temperature of the dialysate introduction circuit 3*a* falls within a predetermined range based on the temperature of the introduced air, for example. Because, as a predetermined amount of the air is introduced to the dialysate filter 10*a*, the temperature of the flow route comes close to the temperature of the introduced air, and a predetermined amount of the dialysate flows in the dialysate circuit 3 in accordance therewith. In this case, a thermometer is provided at an inlet of the primary air introducer 7, for example, and the thermometer measures the temperature of the air introduced into the primary air introducer 7. Meanwhile, another thermometer is also provided at the flow route between the primary air introducer 7 to the dialysate filter 10*a* of the dialysate introduction circuit 3*a*, and the thermometer detects the temperature of the flow route. Both of the detected temperature values are transmitted to the controller 11.

Moreover, the amount of the dialysate flowing in the dialysate circuit 3 may be determined by providing the dialysate introduction circuit 3*a* with a flowmeter. In this case, the flowmeter is provided at an outlet of the dialysate filter 10*a* or at an outlet of the dialysate filter 10*b*. In the case where the flowmeter is provided at the outlet of the dialysate filter 10*b*, the amounts of flow of the dialysate flowing out of the dialysate filter 10*a* and the dialysate filter 10*b* can be measured with a single flowmeter.

Instead of the description made above, the controller 11 may determine whether or not the flow amount of the blood flowing in the blood circuit 2, that is, the amount of blood return reaches the first blood return amount in step S404. The processing to determine whether or not the amount of blood return reaches the first blood return amount may include measuring an amount of rotations of the blood pump 5 and determining whether or not the amount of the blood flowing in the blood circuit 2 reaches the predetermined amount based on the amount of rotations, for example. Note that the flow amount of the dialysate flowing in the dialysate circuit 3 can also be measured in the case of measuring the amount of rotations of the blood pump 5.

Meanwhile, the processing to determine whether or not the amount of blood return reaches the first blood return amount may include measuring the blood thickness in the blood circuit 2 and determining whether or not the blood thickness falls below a predetermined value, for example. Because, the blood thickness in the circuit is reduced in the case where the blood remaining in the blood circuit 2 is returned. In this case, a thickness meter (or a chronometer) is provided in the blood circuit 2, and the thickness meter detects the blood thickness. The detected thickness value is transmitted to the controller 11.

Figure 4:
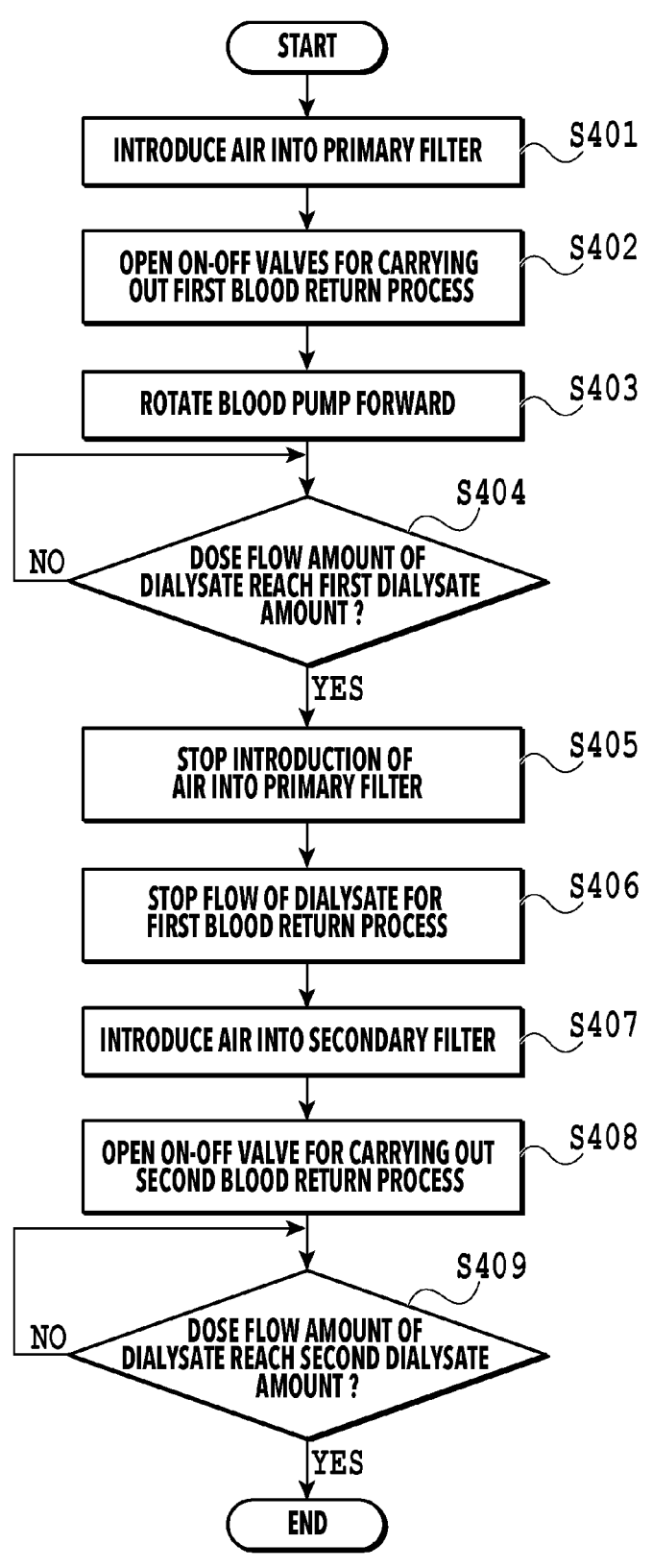
FIG. 4 is a flowchart showing processing according to the first embodiment.

Back to the explanation of FIG. 4, in step S404, the first blood return process is switched to the second blood return process after the determination that the flow amount of the dialysate flowing in the dialysate circuit 3 reaches the first dialysate amount. In step S405, the controller 11 instructs the primary air introducer 7 to stop the introduction of the air into the dialysate filter 10*a*. The on-off valve 7*a* is closed in response to this instruction. Next, the controller 11 instructs the stop of the flow of the dialysate for the first blood return process (step S406). In response to this instruction, the blood pump 5 stops the rotation and the on-off valve V3 and the on-off valve V5 are closed.

Next, the controller 11 instructs the secondary air introducer 8 to introduce the air into the dialysate filter 10*b* (step S407). In response to this instruction, the delivery pump 8*a* of the secondary air introducer 8 rotates and the on-off valve 8*c* and the on-off valve 8*d* are opened, whereby the dialysate filter 10*b* is set to the positive pressure. Next, the controller 11 instructs the on-off valve (the on-off valve V4) for carrying out the second blood return process to be opened (step S408). The on-off valve V4 is opened in response to this instruction. Accordingly, the dialysate stored in the dialysate filter 10*b* flows in the dialysate introduction circuit 3*a*.

As a consequence of the processing from steps S405 to S408, the dialysate flows from the dialysate introduction circuit 3*a* into the blood purifier 1 (the blood purification membrane) and the dialysate pushes out the blood remaining in the blood purifier 1 (the blood purification membrane) toward the blood return side circuit 2*b*, thereby returning the blood to the body (the second blood return process). Here, inside the blood purifier 1, the dialysate flows in the order of the dialysate flow route, the blood purification membrane, and the blood flow route. After step S408, in the case where the controller 11 determines that the flow amount of the dialysate flowing in the dialysate circuit 3 reaches the second dialysate amount (or that the amount of blood return in the blood circuit 2 reaches the second blood return amount) (step S409), the controller 11 instructs the stop of rotation of the delivery pump 8*a* and the like, thereby terminating the operation of the dialysis apparatus 100. The determination of the flow amount of the dialysate or the amount of blood return in step S409 is the same as the determination method described in step S404, and the explanation will be omitted.

The first embodiment has been described above. In the first embodiment, the blood remaining in the blood circuit 2 and the blood purifier 1 (the blood flow route that is not occluded) is first returned to the body in the first blood return process, and then the blood remaining in the blood purifier 1 is returned to the body in the second blood return process. According to the first embodiment, it is possible to recover the blood remaining in the blood circuit 2 by using the less dialysate as compared to the case of carrying out the blood return only in the second blood return process without carrying out the first blood return process. Moreover, it is possible to recover the blood remaining in the occluded blood purifier 1 as compared to the case of carrying out the blood return only in the first blood return process without carrying out the second blood return process.

The first embodiment has described the example of carrying out the blood return by using the dialysate stored in the dialysate filter 10*a* and in the dialysate filter 10*b*. For instance, in a case where a blackout occurs in an environment where the dialysis apparatus 100 is installed, the dialysis apparatus 100 continues to perform minimum functions by using the built-in battery (not shown). However, in a system configuration that operates in coordination with an external apparatus (such as the pure water machine), generation of the new dialysate may be restricted (the dialysate supplier 6 may not be able to generate the dialysate normally) in a case where no batteries are mounted on the external apparatus or in a case where the built-in battery on the dialysis apparatus 100 cannot supply sufficient electric power. In the present embodiment, in the case where a blackout occurs during a dialysis treatment, it is possible to carry out the blood return by using the dialysate stored in the dialysate filter 10*a* and the dialysate filter 10*b* instead of the dialysate from the dialysate supplier 6, by introducing the air from the primary air introducer 7 and the secondary air introducer 8 into the dialysate circuit 3.

Meanwhile, in the first embodiment, the dialysate stored in the dialysate filter 10*a* is used in the first blood return process and the dialysate stored in the dialysate filter 10*b* is used in the second blood return process. Nonetheless, each blood return process may use any amount of the dialysate from any of the filters. The above-described switching from the dialysate filter 10a to the dialysate filter 10b may take place as the need arises.

Second Embodiment

Next, a second embodiment will be described with reference to FIGS. 5 and 6. In the first embodiment, the dialysate from the dialysate circuit 3 that passes through the blood purifier 1 pushes out the blood and the blood is returned to the body of the patient in the second blood return process to be carried out after the first blood return process. In other words, the second blood return process is carried out in the direction from the blood removal side circuit 2a to the blood return side circuit 2b (the normal direction in delivering liquid). In the second embodiment, in addition to the processing described in the first embodiment, the second blood return process in the direction from the blood return side circuit 2b to the blood removal side circuit 2a (the reverse direction in delivering liquid) takes place after carrying out the second blood return process in the normal direction in delivering liquid.

Figure 5:
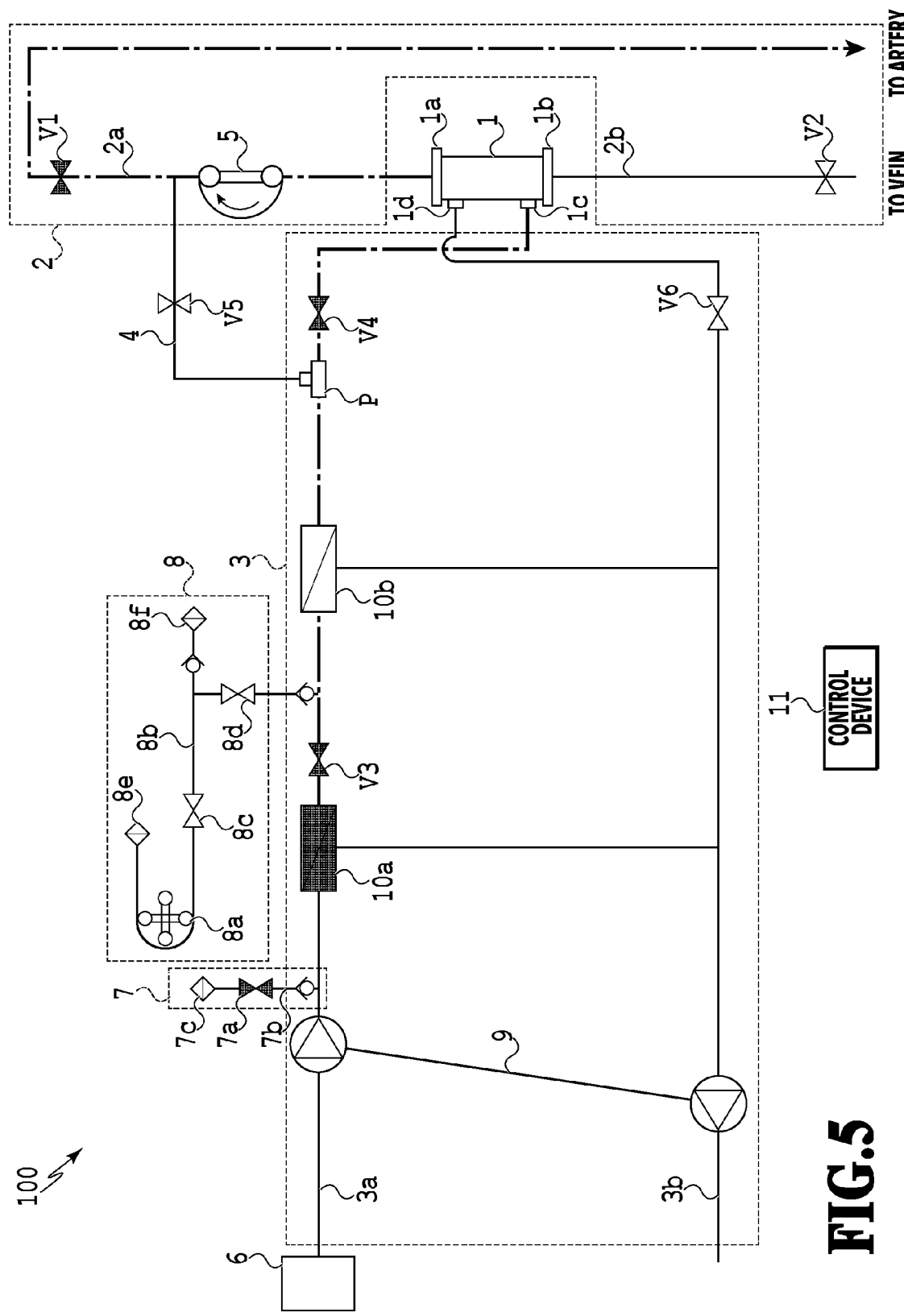
FIG. 5 is a diagram showing a flow of the dialysate in the second blood return process (a reverse direction in delivering liquid)

FIG. 5 shows a flow of the dialysate in the second blood return process in the reverse direction in delivering liquid to be carried out after the second blood return process in the normal direction in delivering liquid.

As shown in FIG. 5, the on-off valve 8c, the on-off valve 8d, and the on-off valve V2 are closed in the case of switching from the second blood return process in the normal direction in delivering liquid to the second blood return process in the reverse direction in delivering liquid. Meanwhile, the delivery pump 8a stops the rotation. On the other hand, the on-off valve 7a, the on-off valve V3, and the on-off valve V1 are opened. Moreover, the blood pump 5 rotates in reverse. By opening the on-off valve 7a, the air is introduced into the dialysate filter 10a and the dialysate filter 10a is set to the atmospheric pressure. Accordingly, the dialysate stored in the dialysate filter 10a flows in the dialysate introduction circuit 3a. By opening the on-off valve V3 and the on-off valve V1 and by the reverse rotation of the blood pump 5, the dialysate passes through the dialysate introduction circuit 3a, the blood purifier 1 (the blood purification membrane), and the blood removal side circuit 2a. Here, the dialysate flows inside the blood purifier 1 in the order of the dialysate flow route, the blood purification membrane, and the blood flow route. In FIG. 5, this flow of the dialysate is indicated with an arrow of a chain line. By this flow of the dialysate, the dialysate that passes through the blood purifier 1 pushes the blood out of the dialysate circuit 3 toward the downstream side in the fluid feeding direction, whereby the blood is returned to the body of the patient.

In the first blood return process and the second blood return process in the normal direction in delivering liquid, the dialysate does not flow in the blood removal side circuit 2a (to be more precise, in a region from a position of connection to the rehydration circuit 4 to a tip end of the blood removal side circuit 2a). As a consequence, it is not possible to sufficiently return the blood remaining in the blood removal side circuit 2a to the body. In the second embodiment, the second blood return process in the reverse direction in delivering liquid is carried out after carrying out the second blood return process in the normal direction in delivering liquid. Accordingly, it is possible to return the blood remaining in the blood removal side circuit 2a to the body.

Next, processing according to the second embodiment will be described with reference to FIG. 6. In the present embodiment, the second blood return process in the reverse direction in delivering liquid is carried out after carrying out the first blood return process and the second blood return process in the normal direction in delivering liquid. The amount of the dialysate necessary for carrying out the first blood return process (the first dialysate amount), the amount of the dialysate necessary for carrying out the second blood return process in the normal direction in delivering liquid (the second dialysate amount), and an amount of the dialysate necessary for carrying out the second blood return process in the reverse direction in delivering liquid are assumed to be determined at a prescribed proportion in advance. In the following, the amount of the dialysate necessary for carrying out the second blood return process in the reverse direction in delivering liquid will be referred to as a "third dialysate amount".

Meanwhile, the amount of blood return to be returned to the body in the first blood return process (the first blood return amount), the amount of blood return to be returned to the body in the second blood return process in the normal direction in delivering liquid (the second blood return amount), and an amount of blood return to be returned to the body in the second blood return process in the reverse direction in delivering liquid may be determined at a prescribed proportion in advance based on the priming volumes of the blood purifier 1 and the blood circuit 2, for example. In the following, the amount of blood return to be returned to the body in the second blood return process in the reverse direction in delivering liquid will be referred to as a "third blood return amount".

Figure 6:
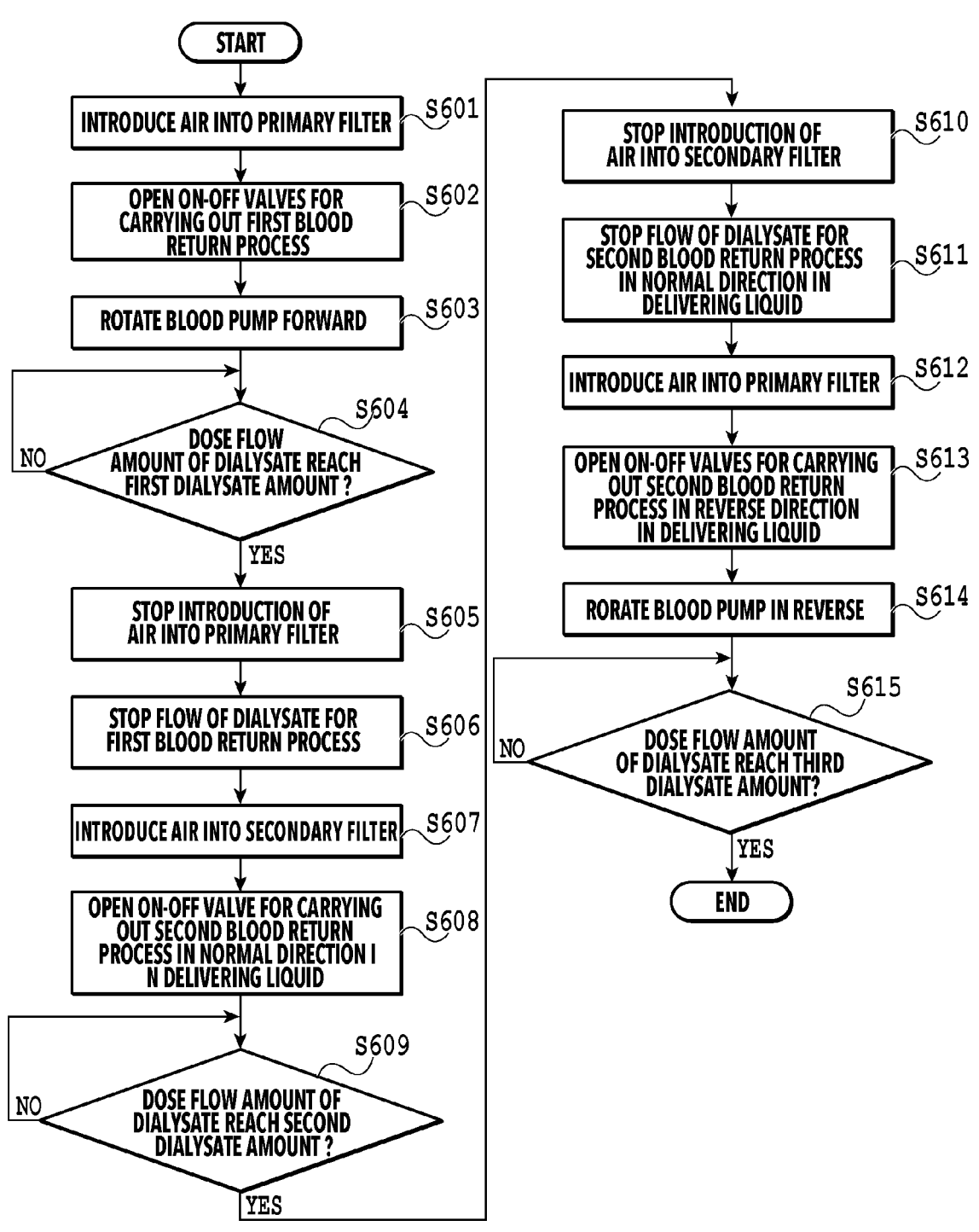
FIG. 6 is a flowchart showing processing according to a second embodiment.

The processing shown in FIG. 6 is equivalent to addition of new processing to the processing shown in FIG. 4. In this regard, the processing from steps S601 to S609 shown in FIG. 6 is the same as the processing from steps S401 to S409 shown in FIG. 4, and explanations thereof will be omitted. In the case where the flow amount of the dialysate flowing in the dialysate circuit 3 is determined to have reached the second dialysate amount in step S609, the second blood return process in the normal direction in delivering liquid is switched to the second blood return process in the reverse direction in delivering liquid.

In the second embodiment, the dialysate stored in the dialysate filter 10a is used in the first blood return process and the second blood return process in the normal direction in delivering liquid, and the dialysate stored in the dialysate filter 10b is used in the second blood return process in the reverse direction in delivering liquid. However, allocation of the dialysate amounts used in the respective processes of the first blood return process, the second blood return process in the normal direction in delivering liquid, and the blood return process in the reverse direction in delivering liquid may be arbitrarily set from the dialysate amounts stored in the dialysate filter 10a and the dialysate filter 10b. The above-described switching from the dialysate filter 10a to the dialysate filter 10b (or from the dialysate filter 10b to the dialysate filter 10a) may take place as the need arises.

In step S610, the controller 11 instructs the secondary air introducer 8 to stop the introduction of the air into the dialysate filter 10b. In response to this instruction, the delivery pump 8a of the secondary air introducer 8 stops the rotation, and the on-off valve 8c and the on-off valve 8d are closed. Next, the controller 11 instructs the stop of the flow of the dialysate for the second blood return process in the normal direction in delivering liquid (step S611). The on-off valve V2 is closed in response to this instruction.

Next, the controller 11 instructs the primary air introducer 7 to introduce the air into the dialysate filter 10a (step S612). In response to this instruction, the on-off valve 7a of the primary air introducer 7 is opened and the dialysate filter 10a is set to the atmospheric pressure.

Next, the controller 11 instructs the on-off valves (the on-off valve V3 and the on-off valve V1) for carrying out the second blood return process in the reverse direction in delivering liquid to be opened (step S613). The on-off valve V3 and the on-off valve V1 are opened in response to this instruction. Next, the controller 11 instructs the blood pump 5 to rotate in reverse (step S614). The blood pump 5 rotates in reverse in response to this instruction. Accordingly, the dialysate stored in the dialysate filter 10a flows in the dialysate introduction circuit 3a.

As a consequence of the processing from steps S609 to S614, the dialysate flows from the dialysate introduction circuit 3a into the blood purifier 1 (the blood purification membrane) and the dialysate pushes out the blood remaining in the blood purifier 1 (the blood purification membrane) toward the downstream side in the fluid feeding direction, thereby returning the blood to the body of the patient (the second blood return process in the reverse direction in delivering liquid). Here, inside the blood purifier 1, the dialysate flows in the order of the dialysate flow route, the blood purification membrane, and the blood flow route. After step S614, in the case where the controller 11 determines that the flow amount of the dialysate flowing in the dialysate circuit 3 reaches the third dialysate amount (or that the amount of blood return in the blood circuit 2 reaches the third blood return amount) (step S615), the controller 11 instructs the stop of rotation of the blood pump 5 and the like, thereby terminating the operation of the dialysis apparatus 100. The determination of the flow amount of the dialysate or the amount of blood return in step S615 is the same as the determination method described in step S404 of the first embodiment, and the explanation will be omitted.

The second embodiment has been described above. In the second embodiment, the blood remaining in the blood circuit 2 is first returned to the body in the first blood return process, then the blood remaining in the blood purifier 1 and the blood circuit 2 is returned from the tip end of the blood return side circuit 2b to the body of the patient in the second blood return process in the normal direction in delivering liquid, and then the blood remaining in the blood purifier 1 and the blood circuit 2 is returned from the blood removal side circuit 2a to the body of the patient in the second blood return process in the reverse direction in delivering liquid. According to the second embodiment, it is possible to recover the blood remaining in the blood removal side circuit 2a as well.

Note that the second blood return process in the reverse direction in delivering liquid takes place after carrying out the second blood return process in the normal direction in delivering liquid in the second embodiment. However, this order may be inverted. Specifically, the second blood return process in the normal direction in delivering liquid may take place after carrying out the first blood return process and the second blood return process in the reverse direction in delivering liquid.

Third Embodiment

Next, a third embodiment will be described with reference to FIGS. 7 to 9. In the first embodiment, in the first blood return process to be carried out in the first place, the dialysate from the dialysate circuit 3 passes through a blood removal side rehydration circuit 4a and the blood removal side circuit 2a, and the blood is returned from the blood return side circuit 2b to the body. In other words, the first blood return process is carried out in the direction from the blood removal side circuit 2a to the blood return side circuit 2b (the normal direction in delivering liquid). In the third embodiment, in addition to the processing described in the first embodiment, the first blood return process in the direction from the blood return side circuit 2b to the blood removal side circuit 2a (the first blood return process in the reverse direction in delivering liquid) takes place after carrying out the first blood return process in the normal direction in delivering liquid. Moreover, the second blood return process (the second blood return process in the normal direction in delivering liquid) takes place after carrying out the first blood return process in the reverse direction in delivering liquid.

Figure 7:
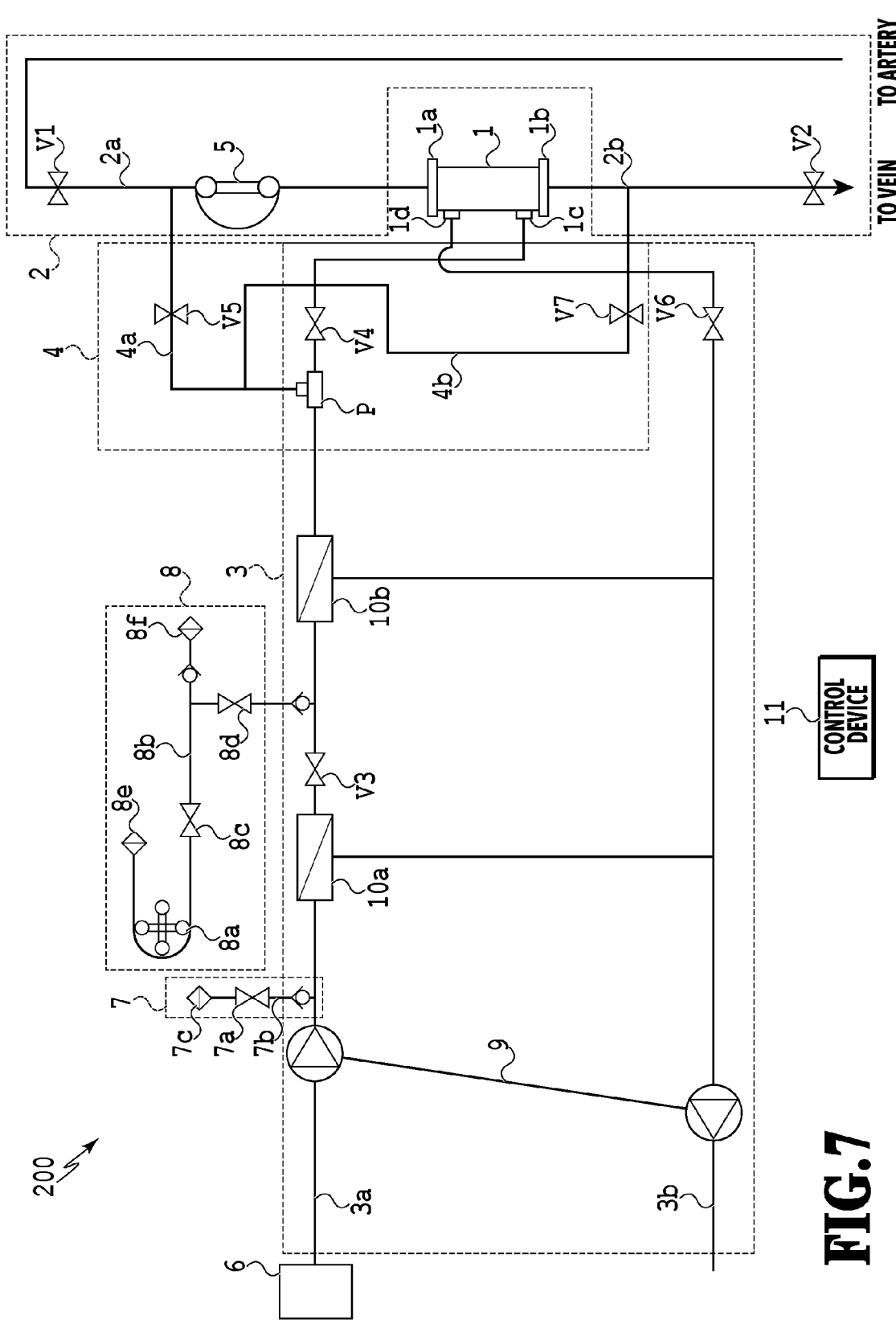
FIG. 7 is an overall configuration diagram of a dialysis apparatus according to a third embodiment.

FIG. 7 is an overall configuration diagram showing a configuration of a dialysis apparatus 200 according to the third embodiment. In the dialysis apparatus 200, the rehydration circuit 4 is different as compared to the dialysis apparatus 100 according to the first embodiment and the second embodiment. Although the rehydration circuit 4 of the dialysis apparatus 100 is the flow route from the dialysate port P to the blood removal side circuit 2a, the rehydration circuit 4 of the dialysis apparatus 200 includes the blood removal side rehydration circuit 4a and a blood return side rehydration circuit 4b. The blood removal side rehydration circuit 4a corresponds to the rehydration circuit 4 of the dialysis apparatus 100.

The blood return side rehydration circuit 4b is a flow route from the dialysate port P to the blood return side circuit 2b for the blood return of the blood in the blood circuit to the patient in accordance with the first blood return process in the reverse direction in delivering liquid. An on-off valve (a Solenoid valve) V7 is disposed at the blood return side rehydration circuit 4b. The flow of the dialysate to the blood return side circuit 2b is controlled by opening and closing the on-off valve V7.

Figure 8:
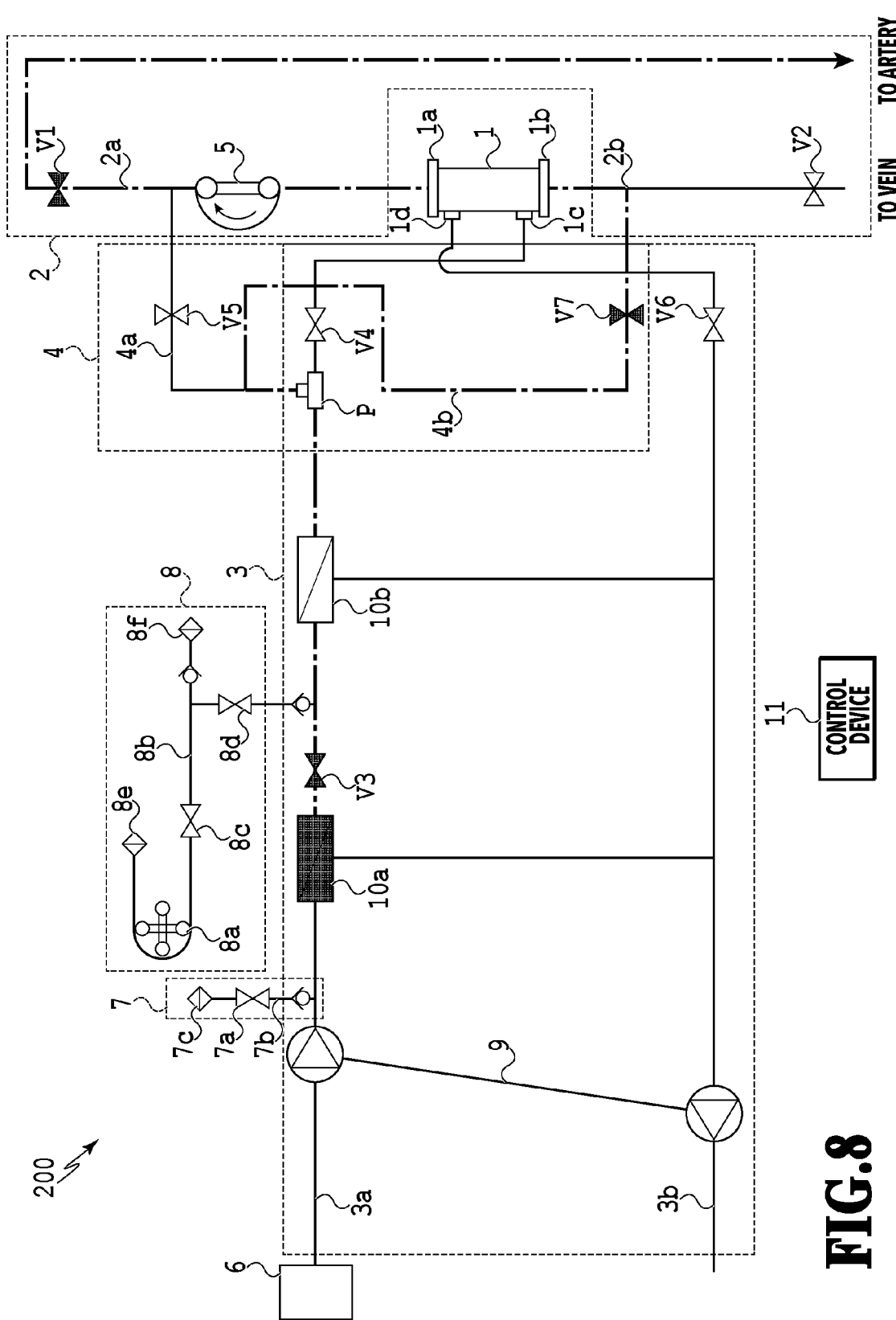
FIG. 8 is a diagram showing a flow of the dialysate in the first blood return process (the reverse direction in delivering liquid)

FIG. 8 shows a flow of the dialysate in the first blood return process in the reverse direction in delivering liquid to be carried out after the first blood return process in the normal direction in delivering liquid.

As shown in FIG. 8, the on-off valve V5 is closed in the case of switching from the first blood return process in the normal direction in delivering liquid to the first blood return process in the reverse direction in delivering liquid. Meanwhile, the blood pump 5 rotates in reverse and the on-off valve V7 is opened. By opening the on-off valve V7 and by the reverse rotation of the blood pump 5, the dialysate passes through the dialysate introduction circuit 3a, the blood return side rehydration circuit 4b, the blood return side circuit 2b, the blood purifier 1 (the blood flow route), and the blood removal side circuit 2a. In FIG. 8, this flow of the dialysate is indicated with an arrow of a chain line. By this flow of the dialysate, the blood remaining in the blood purifier 1 (the blood flow route) and the blood circuit 2 is pushed out, whereby the blood is returned to the body through an artery.

In the first blood return process in the normal direction in delivering liquid, the dialysate does not flow in the blood removal side circuit 2a. As a consequence, it is not possible to sufficiently return the blood remaining in the blood removal side circuit 2a to the body. In the third embodiment, the first blood return process in the reverse direction in delivering liquid takes place after carrying out the first blood return process in the normal direction in delivering liquid. Accordingly, it is possible to return the blood remaining in the blood removal side circuit 2a to the body.

Next, processing according to the third embodiment will be described with reference to FIG. 9. In the present embodiment, the first blood return process in the reverse direction in delivering liquid and the second blood return process in the normal direction in delivering liquid are carried out after carrying out the first blood return process in the normal direction in delivering liquid. The amount of the dialysate necessary for carrying out the first blood return process in the normal direction in delivering liquid (the first dialysate amount), the amount of the dialysate necessary for carrying out the second blood return process (the normal direction in delivering liquid) (the second dialysate amount), and an amount of the dialysate necessary for carrying out the first blood return process in the reverse direction in delivering liquid are assumed to be determined at a prescribed proportion in advance. In the following, the amount of the dialysate necessary for carrying out the first blood return process in the reverse direction in delivering liquid will be referred to as a "fourth dialysate amount".

Meanwhile, the amount of blood return to be returned to the body in the first blood return process in the normal direction in delivering liquid (the first blood return amount), the amount of blood return to be returned to the body in the second blood return process (the normal direction in delivering liquid) (the second blood return amount), and an amount of blood return to be returned to the body in the first blood return process in the reverse direction in delivering liquid may be determined at a prescribed proportion in advance based on the priming volumes of the blood purifier 1 and the blood circuit 2, for example. In the following, the amount of blood return to be returned to the body in the first blood return process in the reverse direction in delivering liquid will be referred to as a "fourth blood return amount".

Figure 9:
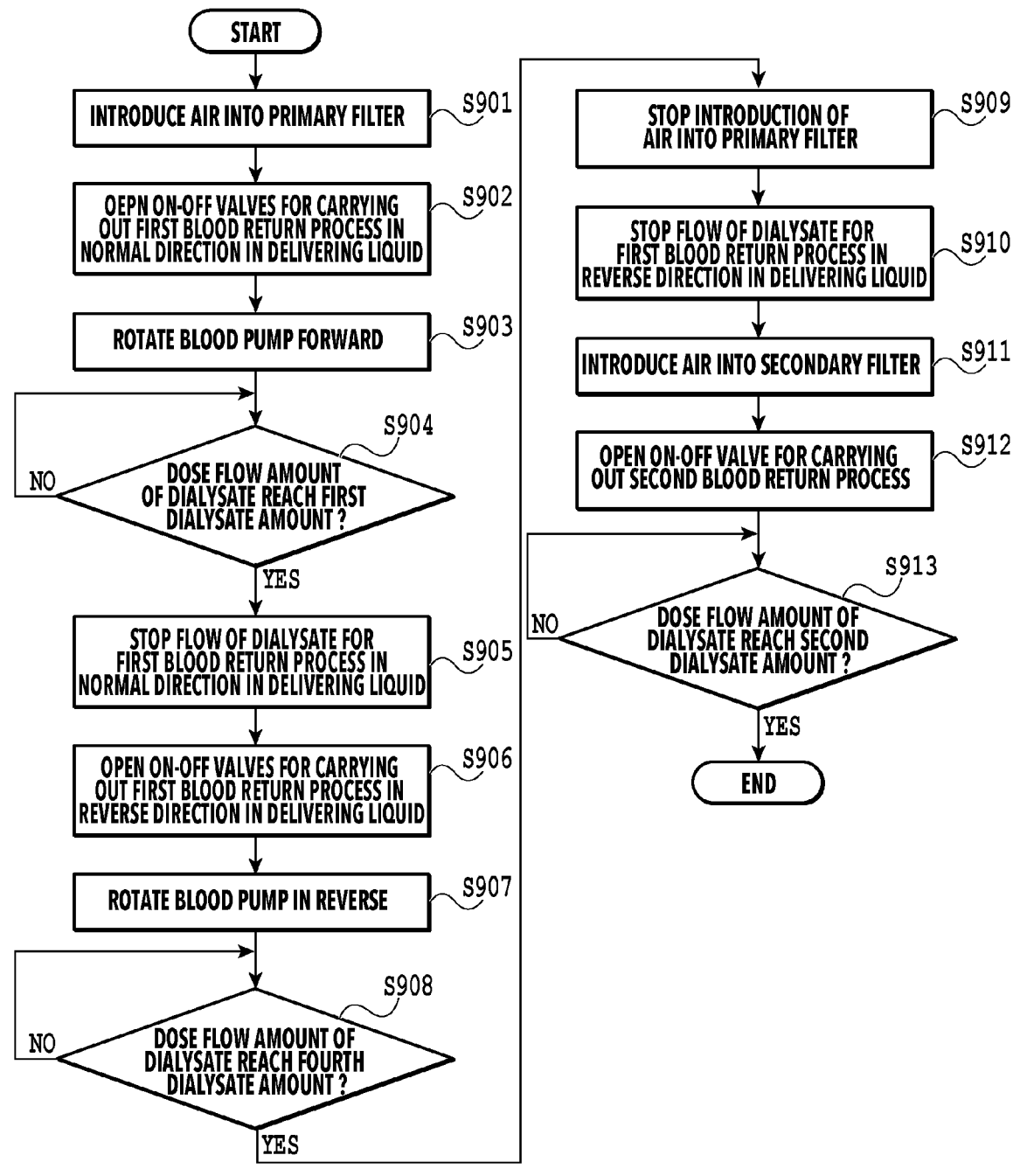
FIG. 9 is a flowchart showing processing according to the third embodiment.

The processing shown in FIG. 9 is equivalent to addition of new processing to the processing shown in FIG. 4. In this regard, the processing from steps S901 to S904 shown in FIG. 9 is the same as the processing from steps S401 to S404 shown in FIG. 4, and explanations thereof will be omitted. In the meantime, the processing from steps S909 to S913 is the same as the processing from steps S405 to S409 shown in FIG. 4, and explanations thereof will be omitted. In the case where the flow amount of the dialysate flowing in the dialysate circuit 3 is determined to have reached the first dialysate amount in step S904, the first blood return process in the normal direction in delivering liquid is switched to the first blood return process in the reverse direction in delivering liquid.

In the third embodiment, the dialysate stored in the dialysate filter 10a is used in the first blood return process in the normal direction in delivering liquid and the first blood return process in the reverse direction in delivering liquid, and the dialysate stored in the dialysate filter 10b is used in the second blood return process. However, allocation of the dialysate amounts used in the respective processes of the first blood return process in the normal direction in delivering liquid, the first blood return process in the reverse direction in delivering liquid, and the second blood return process in the normal direction in delivering liquid may be arbitrarily set from the dialysate amounts stored in the dialysate filter 10a and the dialysate filter 10b. The above-described switching from the dialysate filter 10a to the dialysate filter 10b (or from the dialysate filter 10b to the dialysate filter 10a) may take place as the need arises.

In step S905, the controller 11 instructs the stop of the flow of the dialysate for the first blood return process in the normal direction in delivering liquid. The on-off valve V5 is closed in response to this instruction.

Next, the controller 11 instructs the on-off valves (the on-off valves V1 and V7) for carrying out the first blood return process in the reverse direction in delivering liquid to be opened (step S906). The on-off valves V1 and V7 are opened in response to this instruction. Next, the controller 11 instructs the blood pump 5 to rotate in reverse (step S907). The blood pump 5 rotates in reverse in response to this instruction.

As a consequence of the processing from steps S905 to S907, the dialysate flows from the dialysate introduction circuit 3a into the blood return side rehydration circuit 4b and the blood return side circuit 2b, and the dialysate pushes out the blood remaining in the blood purifier 1 and the blood removal side circuit 2a, thereby returning the blood to the body through the artery (the first blood return process in the reverse direction in delivering liquid). Thereafter, the first blood return process in the reverse direction in delivering liquid is switched to the second blood return process in the case where the controller 11 determines that the flow amount of the dialysate flowing in the dialysate circuit 3 reaches the fourth dialysate amount (or that the amount of blood return in the blood circuit 2 reaches the fourth blood return amount) (step S908). The determination of the flow amount of the dialysate or the amount of blood return in step S908 is the same as the determination method described in step S404 of the first embodiment, and the explanation will be omitted.

The third embodiment has been described above. In the third embodiment, the blood remaining in the blood circuit 2 is first returned from the tip end of the blood return side circuit 2b to the body of the patient in the first blood return process in the normal direction in delivering liquid, and then the blood remaining in the blood circuit 2 is returned from the tip end of the blood removal side circuit 2a to the body in the first blood return process in the reverse direction in delivering liquid. According to the third embodiment, it is possible to recover the blood remaining in the blood removal side circuit 2a as well.

Note that the first blood return process in the reverse direction in delivering liquid takes place after carrying out the first blood return process in the normal direction in delivering liquid in the third embodiment. However, this order may be inverted. Specifically, the first blood return process in the normal direction in delivering liquid and the second blood return process may take place after carrying out the first blood return process in the reverse direction in delivering liquid.

Fourth Embodiment

Next, a fourth embodiment will be described with reference to FIGS. 10 to 13. The first to third embodiments show the example in which only the hemodialysis treatment is intended as the treatment to be carried out before the blood return process. In the fourth embodiment, a hemofiltration treatment, a hemodiafiltration treatment, and so forth are also intended as treatments to be carried out before the blood return process in addition to the hemodialysis treatment. To be more precise, the fourth embodiment is configured to stand on a type of a treatment (a treatment mode) being conducted on the patient, and to carry out the blood return process by selecting any of the first blood return process and the second blood return process after the treatment. Note that the hemodialysis treatment, the hemofiltration treatment, and the hemodiafiltration treatment will be simply referred to in the present embodiment as an HD treatment, an HF treatment, and an HDF treatment, respectively.

Unlike the HD treatment, water, waste products, and electrolytes in the blood are filtered out and removed from the above-described blood purifier as a filtrate in the HF treatment. Instead of the removed filtrate, the dialysate is introduced to dialysate circuit as a replenisher and is injected into the body through the blood circuit. As compared to the HD treatment, the HF treatment has an excellent performance in removing unwanted substances in the body.

The HDF treatment conducts the filtration of the blood and the injection of the replenisher to be carried out in the HF treatment, and introduces the dialysate to be carried out in the HD treatment at the same time. The HDF treatment has an excellent performance in removing a substance with a large molecular weight in the blood as compared to the HD treatment, and has an excellent performance in removing a substance with a small molecular weight in the blood as compared to the HF treatment. In the HDF treatment and the HF treatment, there exist a pre-dilution method designed to inject the replenisher to the upstream of the blood purifier and a post-dilution method designed to inject the replenisher to the downstream of the blood purifier.

In the HF treatment and the HDF treatment according to the post-dilution method, the blood is diluted by injecting the replenisher. Here, the blood in the blood purifier transitions to a concentrated state since the dilution is carried out after the blood passes through the blood purifier. In an example shown in FIGS. 10 to 12, the second blood return process (the reverse direction in delivering liquid) is carried out in order to dilute the blood in the concentrated state, and then the first blood return process (the normal direction in delivering liquid) is carried out. These processes are carried out in the case where a blackout occurs during the HF treatment or the HDF treatment, for example.

Figure 10:
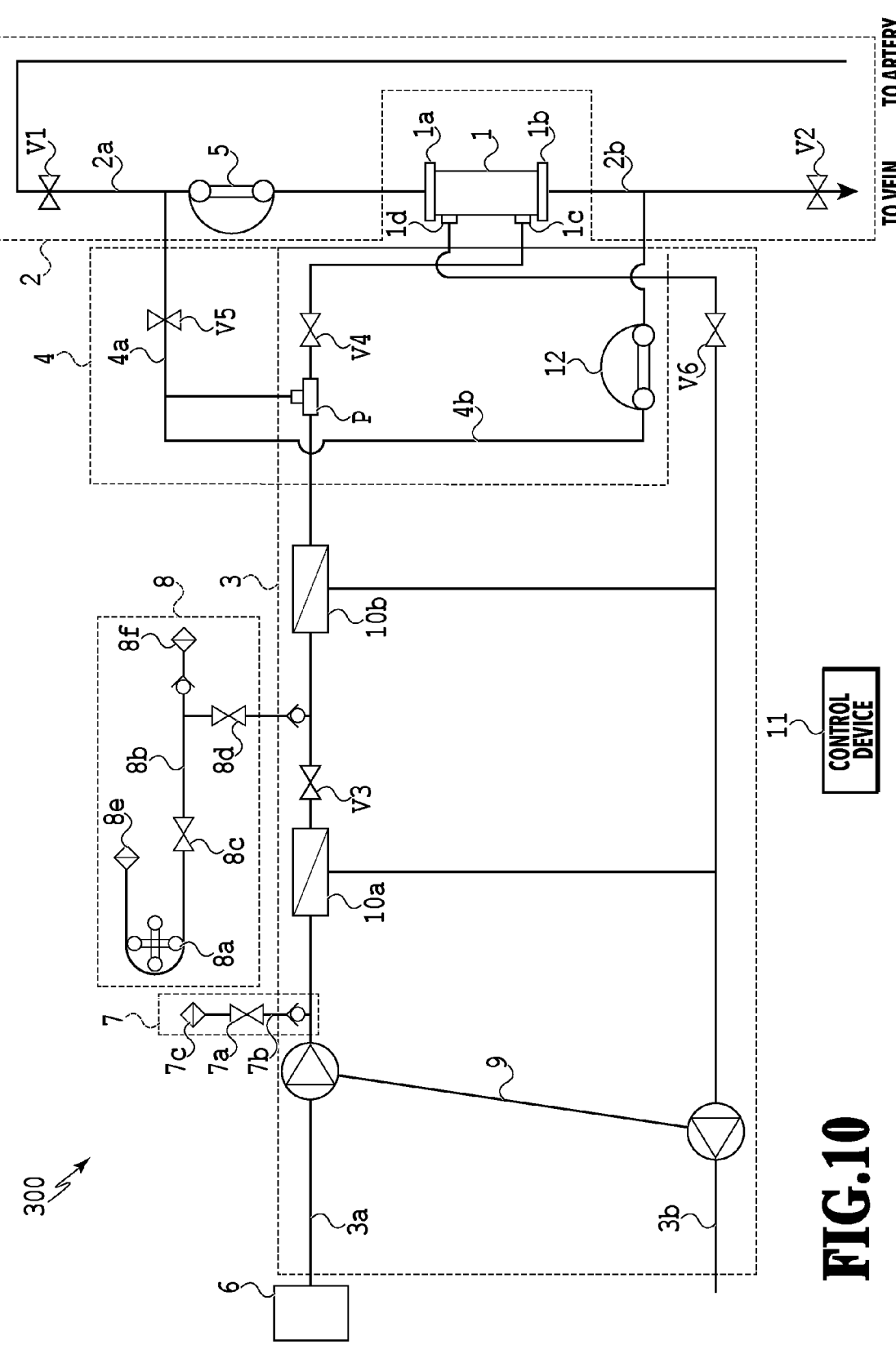
FIG. 10 is an overall configuration diagram of a dialysis apparatus according to a fourth embodiment.

FIG. 10 is an overall configuration diagram showing a configuration of a dialysis apparatus 300 according to the fourth embodiment. In the dialysis apparatus 300, the rehydration circuit 4 includes the blood removal side rehydration circuit 4a and the blood return side rehydration circuit 4b as with the dialysis apparatus 200 according to the third embodiment. The blood removal side rehydration circuit 4a corresponds to the blood removal side rehydration circuit 4a of the dialysis apparatus 200. A rehydration pump 12 is disposed at the blood return side rehydration circuit 4b. The rehydration pump 12 feeds the fluid in a direction to proceed from the blood return side rehydration circuit 4b to the blood return side circuit 2b. The rehydration pump 12 is formed from a peristaltic pump that includes a stator and a rotor. By the forward rotation of the rotor, the blood return side rehydration circuit 4b pinched between the stator and the rotor is squeezed so as to generate the flow toward the blood return side circuit 2b. The flow of the dialysate to the blood return side circuit 2b is controlled by driving the rehydration pump 12.

Although not illustrated, in the HF treatment and the HDF treatment according to the post-dilution method, the dialysate from the dialysate supplier 6 is introduced into the dialysate introduction circuit 3a, passes from the dialysate port P to the blood return side rehydration circuit 4b, and is injected to the blood return side circuit 2b as the replenisher. The blood filtered by the blood purifier 1 is diluted with the replenisher.

Figure 11:
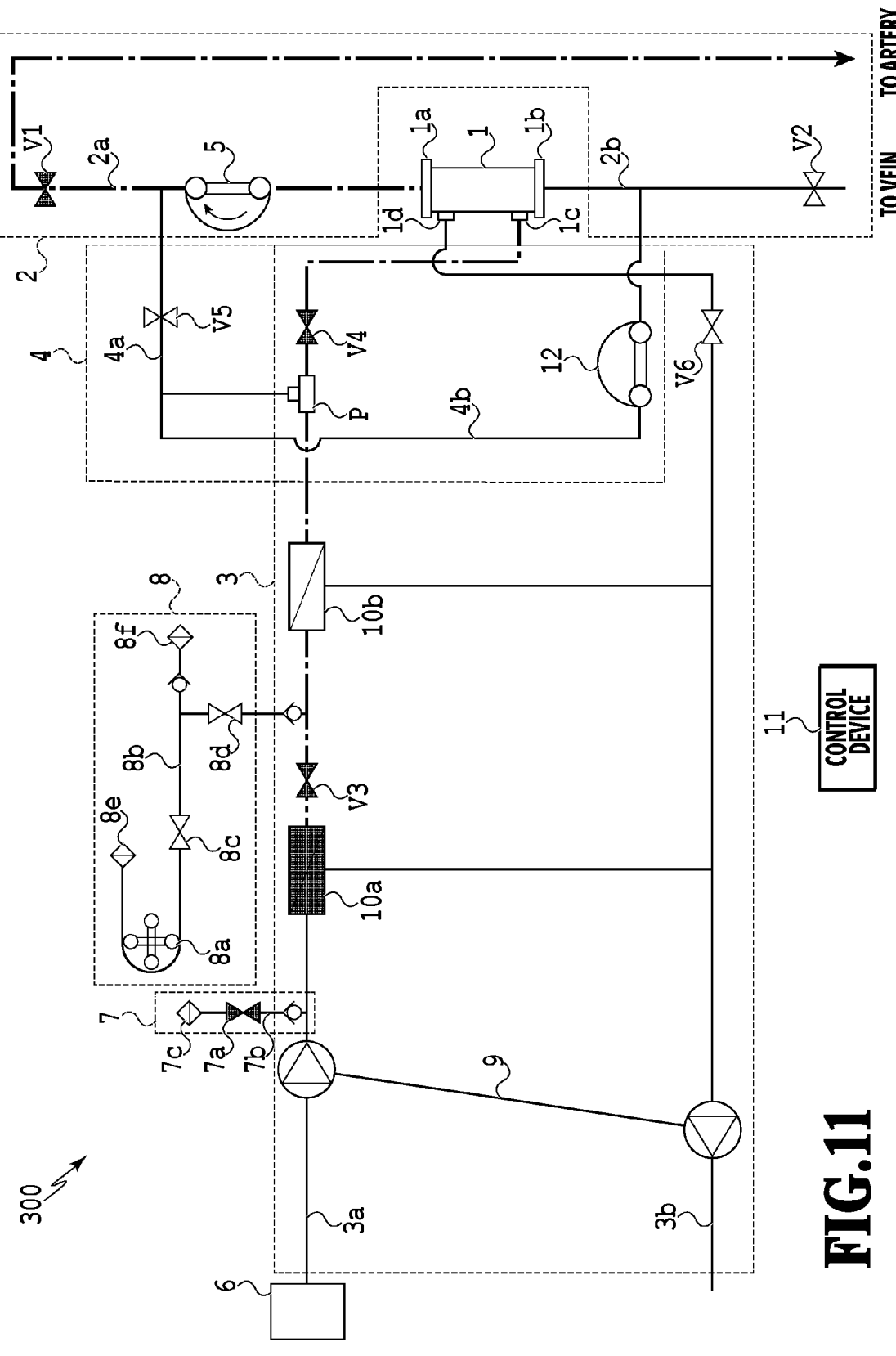
FIG. 11 is a diagram showing a flow of the dialysate in the second blood return process (the reverse direction in delivering liquid)

FIG. 11 shows a flow of the dialysate in the second blood return process in the reverse direction in delivering liquid to be carried out first after the HF treatment or the HDF treatment.

As shown in FIG. 11, the on-off valve 7a, the on-off valve V3, the on-off valve V4, and the on-off valve V1 are opened in the second blood return process. Meanwhile, the blood pump 5 rotates in reverse. By opening the on-off valve 7a, the air is introduced into the dialysate filter 10a, and the dialysate filter 10a is set to the atmospheric pressure. Accordingly, the dialysate stored in the dialysate filter 10a flows in the dialysate introduction circuit 3a. By opening the on-off valve V3, the on-off valve V4, and the on-off valve V1 and by the reverse rotation of the blood pump 5, the dialysate passes through the dialysate introduction circuit 3a, the blood purifier 1 (the blood purification membrane), and the blood removal side circuit 2a. Here, inside the blood purifier 1, the dialysate flows in the order of the dialysate flow route, the blood purification membrane, and the blood flow route. In FIG. 11, this flow of the dialysate is indicated with an arrow of a chain line. By this flow of the dialysate, the dialysate that passes form the dialysate circuit 3 to the blood purifier 1 pushes out the blood to the upstream side in the fluid feeding direction, and the blood is returned to the body of the patient.

Figure 12:
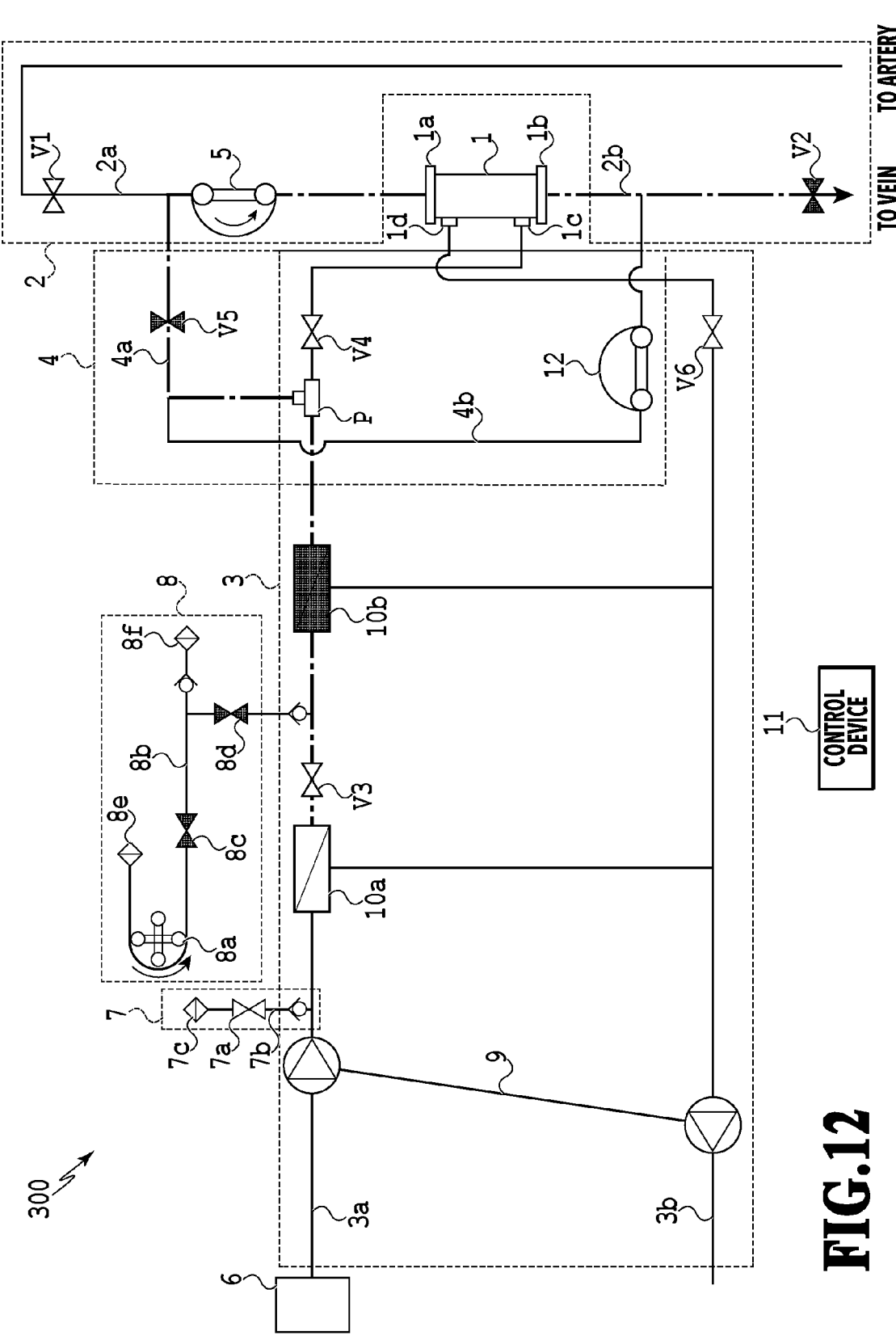
FIG. 12 is a diagram showing a flow of the dialysate in the first blood return process (the normal direction in delivering liquid)

After a predetermined amount of the dialysate flows from the dialysate filter 10a, the second blood return process is switched to the first blood return process. FIG. 12 shows a flow of the dialysate in the first blood return process in the normal direction in delivering liquid to be carried out after the second blood return process.

As shown in FIG. 12, the on-off valve 7a, the on-off valve V3, the on-off valve V4, and the on-off valve V1 are closed in the case where the second blood return process is switched to the first blood return process in the normal direction in delivering liquid. Meanwhile, the delivery pump 8a rotates and the blood pump 5 rotates forward. In the meantime, the on-off valve 8c, the on-off valve 8d, the on-off valve V5, and the on-off valve V2 are opened. By the rotation of the delivery pump 8a and by opening the on-off valve 8c and the on-off valve 8d, the air is introduced into the dialysate filter 10b, and the dialysate filter 10b is set to the positive pressure. Accordingly, the dialysate stored in the dialysate filter 10b flows in the dialysate introduction circuit 3a. By opening the on-off valve V5 and the on-off valve V2 and by the forward rotation of the blood pump 5, the dialysate passes through the dialysate introduction circuit 3a, the blood removal side rehydration circuit 4a, the blood removal side circuit 2a, the blood purifier 1, and the blood return side circuit 2b. In FIG. 12, this flow of the dialysate is indicated with an arrow of a chain line. By this flow of the dialysate, the blood remaining in the blood purifier 1 (the blood flow route) and the blood circuit 2 is pushed out, and the blood is returned to the body through the artery.

As described above, the blood in the blood purifier 1 transitions to the concentrated state in the HF treatment and the HDF treatment (the post-dilution method). Accordingly, by carrying out the second blood return process in the reverse direction in delivering liquid in the first place after the HF treatment and the HDF treatment, the dialysate flows in the blood purification membrane of the blood purifier 1 so that the blood in the blood purifier 1 can be diluted, thereby keeping the blood from transitioning to the concentrated state. In the meantime, the dialysate passes through the blood pump 5 in the second blood return process in the reverse direction in delivering liquid. Thus, it is easier to control the flow amount of the dialysate used for dilution by controlling the rotation of the blood pump.

Figure 13:
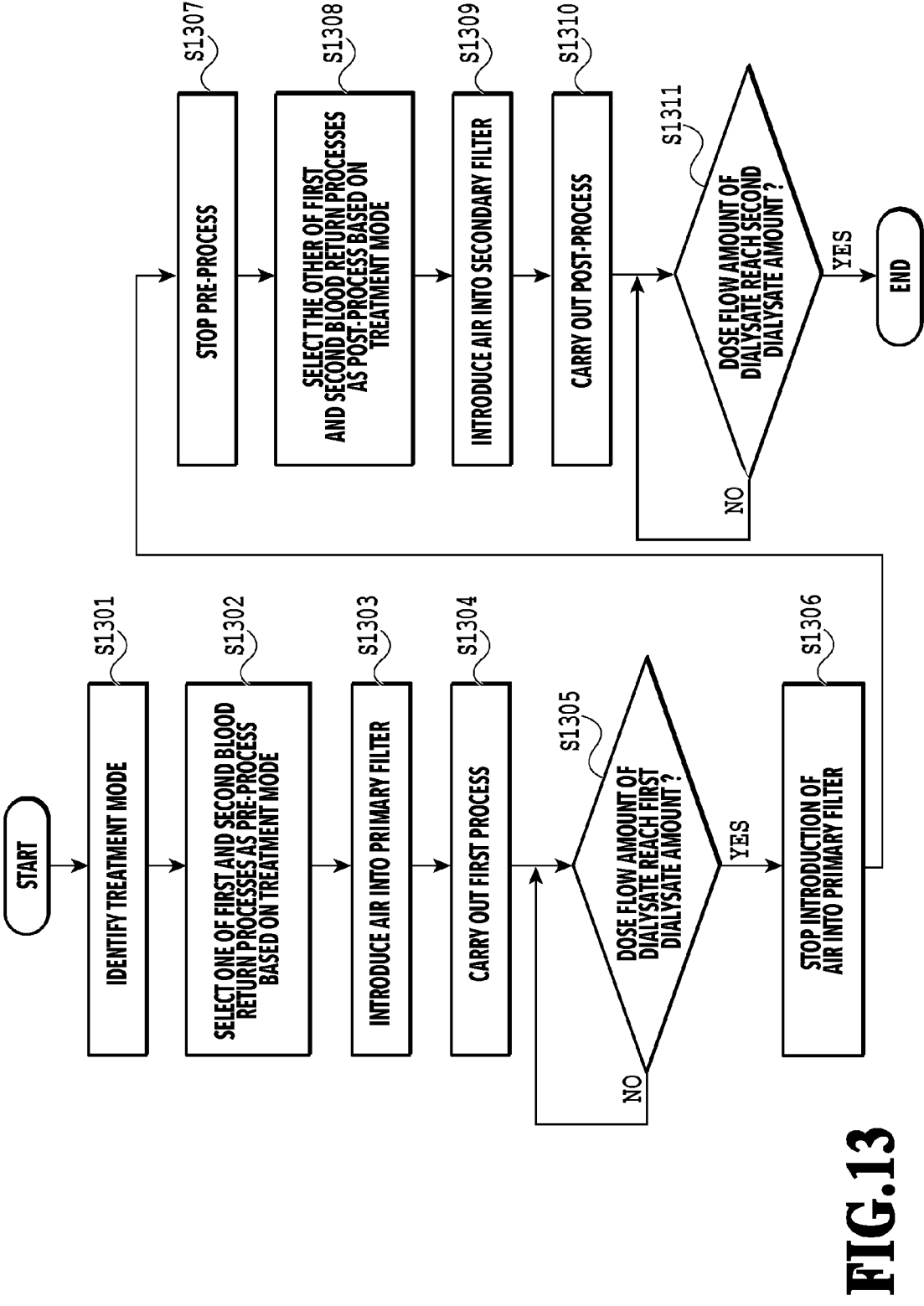
FIG. 13 is a flowchart showing processing according to the fourth embodiment.

Next, processing according to the fourth embodiment will be described with reference to FIG. 13. In the present embodiment, one of the first blood return process and the second blood return process is carried out based on the type of the treatment (a treatment mode) conducted on the patient. Thereafter, the other one of the first blood return process and the second blood return process is carried out. In the example shown in FIG. 13, a blackout occurs in the course of conducting the treatment on the patient in the environment where the dialysis apparatus 300 is installed, and the blood return process is carried out by using the dialysate stored in the dialysate filter 10*a* and the dialysate filter 10*b*. The amount of the dialysate necessary for carrying out the blood return process in the first place (the first dialysate amount) and the amount of the dialysate necessary for carrying out the blood return process thereafter (the second dialysate amount) are assumed to be determined at a prescribed proportion in advance.

The controller is assumed to store a mapping table in a not-illustrated storage device, in which the treatment modes are associated with values indicating the blood return processes to be carried out after the treatments. The mapping table includes data showing the following correspondence relations, for example.

TABLE 1

| Treatment mode | Blood return process 1 (pre-process) | Blood return process 2 (post-process) |
| --- | --- | --- |
| HD treatment | First blood return process (normal direction in delivering liquid) | Second blood return process (normal direction in delivering liquid) |
| HF treatment | Second blood return process (reverse direction in delivering liquid) | First blood return process (normal direction in delivering liquid) |
| HDF treatment | Second blood return process (reverse direction in delivering liquid) | First blood return process (normal direction in delivering liquid) |

The mapping table shown in Table 1 may be stored in the storage device in advance. In this case, the treatment mode is manually selected at the time of starting the treatment, and the corresponding value is stored in the storage device. Instead, the treatment mode and the blood return process may be manually selected at the time of starting the treatment, and the corresponding value may be stored in the storage device.

In step S1301, in response to the occurrence of the blackout in the environment where the dialysis apparatus 300 is installed, the controller 11 identifies the treatment mode corresponding to the treatment being conducted on the patient at that moment. The HF treatment or the HDF treatment is assumed to be conducted in the present embodiment.

Next, the controller 11 refers to the mapping table shown in Table 1, and selects one of the first blood return process and the second blood return process based on the treatment mode identified in step S1301 as the blood return process (a pre-process) to be carried out in the first place (step S1302). In the present embodiment, the second blood return process (the reverse direction in delivering liquid) is assumed to be carried out in the first place corresponding to the HF treatment or the HDF treatment. Note that the second blood return process may be the blood return process in the normal direction in delivering liquid.

Next, the controller 11 instructs the primary air introducer 7 to introduce the air into the dialysate filter 10*a* (step S1303). In response to this instruction, the on-off valve 7*a* of the primary air introducer 7 is opened and the dialysate filter 10*a* is set to the atmospheric pressure.

Next, the controller 11 instructs the on-off valve V3, the blood pump 5, and the like to carry out the pre-process (step S1304). In the present embodiment, the second blood return process in the reverse direction in delivering liquid is carried out in the first place. Accordingly, the controller 11 instructs the on-off valves (the on-off valve V3, the on-off valve V4, and the on-off valve V1) for carrying out the second blood return process to be opened. The on-off valve V3, the on-off valve V4, and the on-off valve V1 are opened in response to this instruction. Meanwhile, the controller 11 instructs the blood pump 5 to rotate in reverse. The blood pump 5 rotates in reverse in response to this instruction. Accordingly, the dialysate stored in the dialysate filter 10*a* flows in the dialysate introduction circuit 3*a*.

By the processing in steps S1303 and S1304, the dialysate flows from the dialysate introduction circuit 3*a* into the blood purifier 1 (the blood purification membrane), thus pushing out the blood that remains in the blood purifier 1 (the blood purification membrane) toward the blood removal side circuit 2*a* and returning the blood to the body (the second blood return process).

Next, the controller 11 determines whether or not the flow amount of the dialysate flowing in the dialysate circuit 3 reaches the first dialysate amount (or the amount of blood return in the blood circuit 2 reaches the first blood return amount) (step S1305). The determination of the flow amount of the dialysate or the amount of blood return in step S1305 is the same as the determination method described in the first embodiment, and the explanation will be omitted. In the case where the flow amount of the dialysate is determined to have reached the first dialysate amount, the controller 11 instructs the primary air introducer 7 to step the introduction of the air into the dialysate filter 10*a* (step S1306). The on-off valve 7*a* is closed in response to this instruction. Next, the controller 11 instructs the stop of the flow of the dialysate for the pre-process (step S1307). In response to this instruction, the blood pump 5 stops the rotation and the on-off valve V3, the on-off valve V4, and the on-off valve V1 are closed.

Next, the controller 11 refers to the mapping table shown in Table 1, and selects the other one of the first blood return process and the second blood return process based on the treatment mode identified in step S1301 as the blood return process (a post-process) to be carried out after the pre-process (step S1308). In the present embodiment, the first blood return process (the normal direction in delivering liquid) is assumed to be carried out as the post-process corresponding to the HF treatment or the HDF treatment.

Note that the first blood return process may be the blood return process in the reverse direction in delivering liquid.

Next, the controller 11 instructs the secondary air introducer 8 to introduce the air into the dialysate filter 10*b* (step S1309). In response to this instruction, the delivery pump 8*a* of the secondary air introducer 8 rotates and the on-off valve 8*c* and the on-off valve 8*d* are opened, whereby the dialysate filter 10*b* is set to the positive pressure.

Next, the controller 11 instructs the on-off valve V5, the blood pump 5, and the like to carry out the post-process (step S1310). In the present embodiment, the first blood return process in the normal direction in delivering liquid is carried out as the post-process. Accordingly, the controller 11 instructs the on-off valves (the on-off valve V5 and the on-off valve V2) for carrying out the first blood return process to be opened. The on-off valve V5 and the on-off valve V2 are opened in response to this instruction. Meanwhile, the controller 11 instructs the blood pump 5 to rotate forward. The blood pump 5 rotates forward in response to this instruction. Accordingly, the dialysate stored in the dialysate filter 10*b* flows in the dialysate introduction circuit 3*a*.

By the processing in steps S1309 and S1310, the dialysate from the dialysate introduction circuit 3*a* flows in the blood removal side rehydration circuit 4*a* and the blood removal side circuit 2*a*, thus pushing out the blood that remains in the blood purifier 1 and the blood return side circuit 2*b* and returning the blood to the body through a vein (the first blood return process in the normal direction in delivering liquid). After step S1310, in the case where the controller 11 determines that the flow amount of the dialysate flowing in the dialysate circuit 3 reaches the second dialysate amount (or the amount of blood return in the blood circuit 2 reaches the second blood return amount) (step S1311), the controller 11 instructs the stop of rotation of the delivery pump 8*a* and so forth, thereby terminating the operation of the dialysis apparatus 300. The determination of the flow amount of the dialysate or the amount of blood return in step S1311 is the same as the determination method described in the first embodiment, and the explanation will be omitted.

The fourth embodiment has been described above. In the fourth embodiment, one of the first blood return process and the second blood return process is selected as the pre-process based on the treatment mode corresponding to the treatment being conducted on the patient. As described above, in the HF treatment and the HDF treatment, the blood in the blood purifier 1 transitions to the concentrated state.

Accordingly, in the case where the treatment being conducted on the patient is the HF treatment or the HDF treatment, it is possible to dilute the blood in the blood purifier 1 and to return the diluted blood to the body by carrying out the second blood return process in the first place.

Meanwhile, as described above, it is possible to recover the blood remaining in the blood circuit 2 by using the less dialysate by carrying out the first blood return process in the first place and then carrying out the second blood return process. The above-described problem of the blood concentration does not occur in the HD treatment. Accordingly, in the case where the treatment being conducted on the patient is the HD treatment, it is possible obtain the above-described advantages by carrying out the first blood return process and the second blood return process in this order.

Note that the blood return processes shown in Table 1 are mere examples. The first blood return process and the second blood return process may be carried out in the optimum order based on the treatment mode corresponding to the treatment being conducted on the patient. Meanwhile, as described in the first to third embodiments, in each of the first blood return process and the second blood return process, the blood return process adopting one of the normal direction in delivering liquid method and the reverse direction in delivering liquid method may be associated with the treatment mode. In the meantime, the blood return process may be associated with the HDF treatment in each of the pre-dilution method and the post-dilution method.

OTHER EMBODIMENTS

In addition to the above-described first to fourth embodiments, the blood return processes may be carried out in sequence shown in the following table, for example. In the fourth embodiment, the blood return processes in sequence shown in Table 2 are associated with the treatment modes. In any of the methods, the amounts of the dialysate necessary for performing the respective blood return processes are determined at a prescribed proportion in advance (or the amounts of blood return to be returned to the body in the respective blood return processes are determined at a prescribed proportion in advance). Here, combinations of the directions of blood return shown in the table are mere examples. It is to be noted that arbitrary blood return methods may be combined in arbitrary sequences without departing from the scope of the invention.

TABLE 2

| Sequence 1 | Sequence 2 | Sequence 3 |
|---|---|---|
| Second blood return process in normal direction in delivering liquid | First blood return process in normal direction in delivering liquid | |
| Second blood return process in reverse direction in delivering liquid | First blood return process in normal direction in delivering liquid | |
| First blood return process in normal direction in delivering liquid | Second blood return process in reverse direction in delivering liquid | |
| First blood return process in reverse direction in delivering liquid | Second blood return process in normal direction in delivering liquid | |
| Second blood return process in normal direction in delivering liquid | Second blood return process in reverse direction in delivering liquid | First blood return process in normal direction in delivering liquid |
| Second blood return process in reverse direction in delivering liquid | Second blood return process in normal direction in delivering liquid | First blood return process in normal direction in delivering liquid |

TABLE 2-continued

| Sequence 1 | Sequence 2 | Sequence 3 |
|---|---|---|
| Second blood return process in normal direction in delivering liquid | First blood return process in normal direction in delivering liquid | First blood return process in reverse direction in delivering liquid |
| Second blood return process in reverse direction in delivering liquid | First blood return process in reverse direction in delivering liquid | First blood return process in normal direction in delivering liquid |

In the above-described first to fourth embodiments, the dialysate stored in the dialysate filter 10*a* and the dialysate filter 10*b* is introduced into the dialysate introduction circuit 3*a*. However, without limitation to this mode, the dialysate generated by the dialysate supplier 6 may be introduced into the dialysate introduction circuit 3*a*. In this case, the controller 11 controls the flow of the dialysate by controlling drive of the dual pump 9. In the above-described processing to determine whether or not the dialysate reaches the first dialysate amount, a determination may be made as to whether or not the flow amount of the dialysate flowing in the dialysate circuit 3 reaches a prescribed amount based on an amount of drive of the dual pump 9 (an amount of rotations of a motor serving as a driving source).

In addition, the above-described first to fourth embodiments are mainly applied to the blood return processes. However, the present disclosure is not limited only to these examples. The above-described processing may also be applied to a rehydration process for preventing a blood pressure drop caused by reduction in blood of the patient due to a water removal process to remove extra water from the blood, and the like. In the rehydration process, the dialysate is injected to the blood circuit so as to supplement the blood in the body.

The above-described embodiments are mere examples. The scope of the present embodiments are not limited only to the described examples. Extra processing and/or constituents may be added to the above-described processing and constituents. Meanwhile, the above-described processing and constituents may be subjected to modifications without departing from the scope of the invention. Alternatively, a specific part of the above-described processing and constituents may be omitted. Moreover, the described order of processing may be changed. In the meantime, instead of exclusively switching between the first blood return process and the second blood return process, the blood return process may be carried out in a state of coexistence of (overlapping) the first blood return process and the second blood return process for a certain period.

Incidentally, the dialysis apparatus according to the embodiments is implemented by a computer program to be executed by the controller 11. Here, the computer program may be stored in a non-transitory storage medium. Examples of the non-transitory storage medium include a read only memory (ROM), a random access memory (RAM), a register, a cache memory, a semiconductor memory device, a magnetic medium such as a built-in hard disk drive and a removable disk drive, a magneto-optical medium, an optical medium such as a CD-ROM disc and a digital versatile disc (DVD), and so forth.

The above-described embodiments are applied to a blood purification apparatus which at least includes a blood circuit, a dialysate circuit, and a controller, and is configured return blood remaining in the blood circuit to a body.

REFERENCE SIGNS LIST 1 blood purifier
1*a* blood introduction inlet
1*b* blood introduction outlet
1*c* dialysate introduction inlet
1*d* dialysate drainage port
2 blood circuit
2*a* blood removal side circuit
2*b* blood return side circuit
3 dialysate circuit
3*a* dialysate introduction circuit
3*b* dialysate drainage circuit
4 rehydration circuit
4*a* blood removal side rehydration circuit
4*b* blood return side rehydration circuit
5 blood pump
6 dialysate supplier
7 primary air introducer
7*a* on-off valve
7*b* air flow route
8 secondary air introducer
8*a* delivery pump
8*b* air flow route
8*c* on-off valve
8*d* on-off valve
8*e* air filter
8*f* air filter
9 dual pump
10*a* dialysate filter
10*b* dialysate filter
11 controller
12 rehydration pump
P dialysate port
V1 to V7 on-off valve

The invention claimed is:

1. A blood purification apparatus comprising:
a blood circuit and a dialysate circuit configured to bidirectionally circulate a fluid through a blood purification membrane of a blood purifier; and
a controller,
wherein the blood circuit and the dialysate circuit include:
    a first flow route that causes a dialysate to flow from the dialysate circuit into the blood circuit through a connection flow route that connects the dialysate circuit to the blood circuit while bypassing the blood purifier, and
    a second flow route that causes the dialysate to flow from the dialysate circuit into the blood circuit through the blood purification membrane,
wherein the blood circuit comprises a first pump;
wherein the dialysate circuit is attached to an air introducer that comprises a second pump and a first valve,
wherein the connection flow route comprises a second valve;
wherein the controller is configured to:
    perform control such that the first valve closes, the second valve opens, the first pump performs a first rotation, the second pump stops a second rotation, and blood in the blood circuit is returned to a body by feeding the dialysate to one of the first flow route and the second flow route, determine whether or not a flow amount of the dialysate reaches a predetermined flow amount, and perform control such that the first valve opens, the second valve closes, the first pump stops the first rotation, the second pump performs the second rotation, and the blood in the blood circuit is returned to the body by feeding the dialysate to an other one of the first flow route and the second flow route in response to determination that the flow amount of the dialysate reaches the predetermined flow amount.

2. The blood purification apparatus according to claim 1, further comprising:

a dialysate supplier that supplies the dialysate to the dialysate circuit; and a dialysate filter that stores the dialysate supplied from the dialysate supplier, wherein the controller performs control such that the dialysate returns the blood in the blood circuit to the body by feeding the dialysate stored in the dialysate filter to the one of the first flow route and the second flow route in a state where the dialysate supplier does not supply the dialysate to the dialysate circuit.

3. The blood purification apparatus according to claim 1, wherein the first flow route further includes a flow route that causes the dialysate to flow from the dialysate circuit into a blood removal side circuit and a blood return side circuit through the connection flow route, and the second flow route further includes a flow route that causes the dialysate to flow from the dialysate circuit into the blood return side circuit.

4. The blood purification apparatus according to claim 1, wherein the first flow route further includes a flow route that causes the dialysate to flow from the dialysate circuit into a blood return side circuit and a blood removal side circuit through the connection flow route, and the second flow route further includes a flow route that causes the dialysate to flow from the dialysate circuit into the blood removal side circuit.

5. The blood purification apparatus according to claim 1, wherein the first flow route further includes a flow route that causes the dialysate to flow from the dialysate circuit into a blood removal side circuit and a blood return side circuit through the connection flow route, the blood circuit and the dialysate circuit further include a third flow route that causes the dialysate to flow from the dialysate circuit into the blood return side circuit and the blood removal side circuit through the connection flow route while bypassing the blood purifier, the controller performs control such that the blood in the blood circuit is returned to the body by feeding the dialysate to one of the first flow route and the third flow route, the controller determines whether or not the flow amount of the dialysate reaches a predetermined second flow amount, and the controller performs control such that the blood in the blood circuit is returned to the body by feeding the dialysate to the other one of the first flow route and the third flow route in response to determination that the flow amount of the dialysate reaches the predetermined second flow amount.

6. The blood purification apparatus according to claim 1, wherein the second flow route further includes a flow route that causes the dialysate to flow from the dialysate circuit into a blood return side circuit, the blood circuit and the dialysate circuit further include a fourth flow route that causes the dialysate to flow from the dialysate circuit into a blood removal side circuit through the blood purification membrane, the controller performs control such that the blood in the blood circuit is returned to the body by feeding the dialysate to one of the second flow route and the fourth flow route, the controller determines whether or not the flow amount of the dialysate reaches a predetermined third flow amount, and the controller performs control such that the blood in the blood circuit is returned to the body by feeding the dialysate to the other one of the second flow route and the fourth flow route in response to determination that the flow amount of the dialysate reaches the predetermined third flow amount.

7. The blood purification apparatus according to claim 1, wherein after a blood purification treatment in a prescribed treatment mode, the controller selects one of the first flow route and the second flow route as a flow route for the dialysate based on the treatment mode in order to return the blood in the blood circuit to the body.

8. The blood purification apparatus according to claim 7, wherein in a case where the treatment mode indicates any of a hemofiltration treatment and a hemodiafiltration treatment, the controller performs control such that the blood in the blood circuit is returned to the body by selecting the second flow route as the flow route for the dialysate and feeding the dialysate to the second flow route, and the controller performs control such that the blood in the blood circuit is returned to the body by feeding the dialysate to the first flow route in response to the determination that the flow amount of the dialysate reaches the predetermined flow amount.

9. A blood purification apparatus comprising:

a blood circuit and a dialysate circuit configured to bidirectionally circulate a fluid through a blood purification membrane of a blood purifier; and a controller, wherein the blood circuit and the dialysate circuit include:

a first flow route that causes a dialysate to flow from the dialysate circuit into the blood circuit through a connection flow route that connects the dialysate circuit to the blood circuit while bypassing the blood purifier, and a second flow route that causes the dialysate to flow from the dialysate circuit into the blood circuit through the blood purification membrane, wherein the blood circuit comprises a first pump, wherein the dialysate circuit is attached to an air introducer that comprises a second pump and a first valve, wherein the connection flow route comprises a second valve, wherein the controller is configured to:

perform control such that the first valve closes, the second valve opens, the first pump performs a first rotation, the second pump stops a second rotation, and blood in the blood circuit is returned to a body by feeding the dialysate to one of the first flow route and the second flow route, determine whether or not a return flow amount of the blood reaches a predetermined blood return amount, and perform control such that the first valve opens, the second valve closes, the first pump stops the first rotation, the second pump performs the second rotation and the blood in the blood circuit is returned to the body by feeding the dialysate to an other one of the first flow route and the second flow route in response to determination that the blood return amount of the blood reaches the predetermined blood return amount.

10. A method to be executed by a blood purification apparatus provided with a blood circuit and a dialysate circuit configured to bidirectionally circulate a fluid through a blood purification membrane of a blood purifier, and a controller, the blood circuit and the dialysate circuit including a first flow route that causes a dialysate to flow from the dialysate circuit into the blood circuit through a connection flow route that connects the dialysate circuit to the blood circuit while bypassing the blood purifier, and a second flow route that causes the dialysate to flow from the dialysate circuit into the blood circuit through the blood purification membrane, and the blood circuit comprising a pump, the method comprising steps of:

causing the controller to perform control such that the pump performs a rotation and blood in the blood circuit is returned to a body by feeding the dialysate to one of the first flow route and the second flow route;

causing the controller to determine whether or not a flow amount of the dialysate reaches a predetermined flow amount; and causing the controller to perform control such that the pump stops the rotation and the blood in the blood circuit is returned to the body by feeding the dialysate to an other one of the first flow route and the second flow route in response to determination that the flow amount of the dialysate reaches the predetermined flow amount.

11. A method to be executed by a blood purification apparatus provided with a blood circuit and a dialysate circuit configured to bidirectionally circulate a fluid through a blood purification membrane of a blood purifier, and a controller, the blood circuit and the dialysate circuit including a first flow route that causes a dialysate to flow from the dialysate circuit into the blood circuit through a connection flow route that connects the dialysate circuit to the blood circuit while bypassing the blood purifier, and a second flow route that causes the dialysate to flow from the dialysate circuit into the blood circuit through the blood purification membrane, and the blood circuit comprising a pump, the method comprising steps of:

causing the controller to perform control such that the pump performs a rotation and blood in the blood circuit is returned to a body by feeding the dialysate to one of the first flow route and the second flow route;

causing the controller to determine whether or not a return flow amount of the blood reaches a predetermined blood return amount; and causing the controller to perform control such that the pump stops the rotation and the blood in the blood circuit is returned to the body by feeding the dialysate to an other one of the first flow route and the second flow route in response to determination that the blood return amount of the blood reaches the predetermined blood return amount.

* * * * *